US008265952B1

(12) United States Patent
Smith

(10) Patent No.: US 8,265,952 B1
(45) Date of Patent: Sep. 11, 2012

(54) METHOD AND SYSTEM FOR HEALTH CARE CODING TRANSITION AND IMPLEMENTATION

(75) Inventor: Joseph S. Smith, Little Rock, AR (US)

(73) Assignee: Arkansas Blue Cross and Blue Shield, Little Rock, AR (US)

( * ) Notice: Subject to any disclaimer, the term of this patent is extended or adjusted under 35 U.S.C. 154(b) by 213 days.

(21) Appl. No.: 12/710,787

(22) Filed: Feb. 23, 2010

Related U.S. Application Data

(60) Provisional application No. 61/202,364, filed on Feb. 23, 2009.

(51) Int. Cl.
*G06Q 50/00* (2012.01)
(52) U.S. Cl. .................................. 705/2; 705/4
(58) Field of Classification Search .......... 704/9; 707/1, 707/4; 705/2–4
See application file for complete search history.

(56) References Cited

U.S. PATENT DOCUMENTS

| | | | | |
|---|---|---|---|---|
| 6,915,254 | B1 * | 7/2005 | Heinze et al. | 704/9 |
| 7,624,027 | B1 * | 11/2009 | Stern et al. | 705/2 |
| 7,664,660 | B2 * | 2/2010 | Korpman et al. | 705/2 |
| 7,716,072 | B1 * | 5/2010 | Green et al. | 705/3 |
| 7,720,691 | B2 * | 5/2010 | Hasan et al. | 705/2 |
| 7,827,234 | B2 * | 11/2010 | Eisenberger et al. | 709/203 |
| 7,908,293 | B2 * | 3/2011 | Aronson et al. | 707/791 |
| 8,050,938 | B1 * | 11/2011 | Green et al. | 705/2 |
| 2004/0220895 | A1 * | 11/2004 | Carus et al. | 707/1 |
| 2008/0306926 | A1 * | 12/2008 | Friedlander et al. | 707/4 |

* cited by examiner

*Primary Examiner* — Gerald J. O'Connor
*Assistant Examiner* — Natalie A Pass
(74) *Attorney, Agent, or Firm* — Arent Fox LLP

(57) ABSTRACT

Methods and systems for implementing coding changes for a transaction are provided. At least one transaction in an original format is received and normalized into a different format. The normalized transaction may be processed and the processing results may be associated with the original format to transmit the processing results in the original format to a recipient.

19 Claims, 32 Drawing Sheets

200

202 Receiving transaction information/data

204 Determining whether the code of the received transaction information/data maps to a single code 206 No → FIG. 2B Yes 208 Mapping the received information/data to the code associated with the system 210 Storing the received transaction information/data and the mapped transaction information/data End

FIG. 2A

ICD 10 CODE LOOKUP

Home | Help
- ICD 10 MAPPINGS
  - ICD-10 code lookup
  - Manage ICD-10 Mappings
- ICD 10 CLAIM MAPPINGS
- ICD 10 REPORTS
- CLAIM REPORTS
- CONFIGURATION

ENTER VALID ICD10 DX/PCS CODE

DX⦿ PCS⦿    [Display Mappings]

ICD 10 CODE: L8944   Pressure ulcer of contiguous site of back buttock and hip stage IV

ICD 10 - ICD 9 ACTIVE MAPPINGS FOR ICD10 CODE - L8944

L8944           : PRESSURE ULCER OF CONTIGUOUS SITE OF BACK, BUTTOCK AND HIP, STAGE IV
MAPPING TYPE    : CMS
USER CREATE ID  : CMS
CLUSTER         : YES
MAP EFF DATE    : DATE

| ICD 9 CODE | POSITION | CODE DESCRIPTION |
|---|---|---|
| 70703 | P | PRESSURE ULCER, LOW BACK |
| 70704 | 1 | PRESSURE ULCER, HIP |
| 70704 | 2 | PRESSURE ULCER, HIP |
| 70724 | 3 | PRESSURE ULCER STAGE IV |

Welcome admin | logout

SEARCH CLAIM BY DATE RANGE

Select the start date
Select the end date

336

[Search]

CLAIMS LOOK UP BY DATE

Calendar widget: Today, Sun Mon Tue Wed Thu Fri Sat

Select data

CLAIMS FROM 2010-01-1 TO 2010-01-9 DETAILS

| LOB | ICN NUMBER | AHIN NUMBER | MEMBER ID | CLAIM SEQ NUMBER | CLAIM STATUS CODE | ADDITIONAL FILE | FILE IN DATE |
|---|---|---|---|---|---|---|---|
| ABCBS | 1234567890b | 1111111111b | 4445566667 | 1 | Normalized | ABCBS.FF_837_I ABCBS.FF_837_P | Date |
| ABCBS | 1234567890a | 1111111111a | 1000000006 | 1 | Normalized | ABCBS.FF_837_I ABCBS.FF_837_P | Date |
| ABCBS | 1234567890c | 1111111111c | 1000000004 | 1 | Normalized | ABCBS.FF_837_I ABCBS.FF_837_P | Date |
| ABCBS | 1234567890d | 1111111111d | 1000000003 | 1 | Normalized | ABCBS.FF_837_I ABCBS.FF_837_P | Date |
| ABCBS | 1234567890e | 1111111111e | 1000000005 | 1 | Normalized | ABCBS.FF_837_I ABCBS.FF_837_P | Date |
| ABCBS | 2345678901b | 2222222222b | 1000000003 | 1 | Normalized | ABCBS.FF_837_I ABCBS.FF_837_P | Date |
| ABCBS | 2345678901a | 2222222222a | 1000000001 | 1 | Normalized | ABCBS.FF_837_I ABCBS.FF_837_P | Date |
| ABCBS | 1234567890 | 1111222233 | 1234567890 | 1 | Normalized | ABCBS.FF_837_I ABCBS.FF_837_P | Date |
| ABCBS | 2345678901 | 2222222222 | 4445566667 | 1 | Normalized | ABCBS.FF_837_I ABCBS.FF_837_P | Date |
| ABCBS | 3456789012 | 3333333333 | 1000000003 | 1 | Normalized | ABCBS.FF_837_I ABCBS.FF_837_P | Date |
| ABCBS | 4567890123 | 4444444444 | 1000000004 | 1 | Normalized | ABCBS.FF_837_I ABCBS.FF_837_P | Date |
| ABCBS | 5678901234 | 5555555555 | 1000000005 | 1 | Normalized | ABCBS.FF_837_I ABCBS.FF_837_P | Date |
| ABCBS | 6789012345 | 2345678577 | 1111444436 | 1 | Normalized | ABCBS.FF_837_I | Date |
| ABCBS | 7890123456 | 7777777777 | 1000000007 | 1 | Normalized | ABCBS.FF_837_I | Date |

338

Home | Help
▶ ICD 10 MAPPINGS
▼ ICD 10 CLAIM MAPPINGS
   Claim lookup - ICN/AHIN/MEMBER ID
   Claim lookup - Dates
   Claim lookup - Files
▶ ICD 10 REPORTS
▶ CLAIM REPORTS
▶ CONFIGURATION Welcome admin | logout

FIG. 3E

Home | Help
- ICD 10 MAPPINGS
- ICD 10 CLAIM MAPPINGS
  - Claim lookup - ICN/AHIN/MEMBER-ID
  - Claim lookup - Dates
  - Claim lookup - Files
- ICD 10 REPORTS
- CLAIM REPORTS
- CONFIGURATION Welcome admin | logout

CLAIMS LOOK UP BY FILE

SEARCH CLAIMS BY FILENAME

Enter the filename [ABCBS.FF_837_P_]  [Search]

— 340

CLAIMS IN ABCBS.FF_837_P_TESTFILE.01012010 FILE

| LOB | ICN NUMBER | AHIN NUMBER | MEMBER ID | CLAIM SEQ. NUMBER | CLAIM STATUS CODE | ADDITIONAL FILE NAME | FILE IN DATE |
|---|---|---|---|---|---|---|---|
| ABCBS | 1234567890e | 1111111111e | 1000000005 |  | Normalized | ABCBS.FF_837_P_ | Date |
| ABCBS | 1234567890c | 1111111111c | 1000000003 | 1 | Normalized | ABCBS.FF_837_P_ | Date |
| ABCBS | 1234567890d | 1111111111d | 1000000004 |  |  |  |  |
| ABCBS | 1234567890a | 1111111111a | 1000000006 | 1 | Normalized | ABCBS.FF_837_P_ | Date |
| ABCBS | 1234567890b | 1111111111b | 4445556667 | 1 | Normalized | ABCBS.FF_837_P_ | Date |
| ABCBS | 1234567890 | 1111222233 | 1234567801 | 1 | Normalized | ABCBS.FF_837_P_ | Date |

Home | Help                                                                                                          Welcome admin | logout

- ICD 10 MAPPINGS
- ICD 10 CLAIM MAPPINGS
- ICD 10 REPORTS
  - ICD 9 to ICD 10 Mappings
  - NODX Codes
  - User Change History
  - ICD 10 Change History-Dates
  - Active CMS Mappings
  - NODX - Change History
  - ICD 10 Effective Dates
  - ICD 10 Codes Status
- CLAIM REPORTS
- CONFIGURATION

MAPPED ICD 10 CODES TO AN ICD 9 CODE

ENTER VALID ICD 9 DX/PCS CODE

[ICD9 Code]   DX ● PROC ○   [Display Mappings]

70704 CODE AS PRINCIPLE DIAGNOSIS

| I10 CODE | CODE DESCRIPTION | CODE TYPE | MAP EFF. DATE | MAP TERM. DATE | STATUS | COMMENTS |
|---|---|---|---|---|---|---|
| L89201 | Pressure ulcer of unspecified hip, stage I | ICD10_DX | Date | Date | Active | CMS updated |
| L89202 | Pressure ulcer of unspecified hip, stage II | ICD10_DX | Date | Date | Active | CMS updated |
| L89203 | Pressure ulcer of unspecified hip, stage III | ICD10_DX | Date | Date | Active | CMS updated |
| L89204 | Pressure ulcer of unspecified hip, stage IV | ICD10_DX | Date | Date | Active | CMS updated |
| L89209 | Pressure ulcer of unspecified hip, unspecified stage | ICD10_DX | Date | Date | Active | CMS updated |
| L89211 | Pressure ulcer of right hip, stage I | ICD10_DX | Date | Date | Active | CMS updated |
| L89212 | Pressure ulcer of right hip, stage II | ICD10_DX | Date | Date | Active | CMS updated |
| L89213 | Pressure ulcer of right hip, stage III | ICD10_DX | Date | Date | Active | CMS updated |
| L89214 | Pressure ulcer of right hip, stage IV | ICD10_DX | Date | Date | Active | CMS updated |

70704 CODE AS FIRST ADDITIONAL

| I10 CODE | CODE DESCRIPTION | CODE TYPE | MAP EFF. DATE | MAP TERM. DATE | STATUS | COMMENTS |
|---|---|---|---|---|---|---|
| L8944 | Pressure ulcer of contiguous site of back, buttock and hip, stage IV | ICD10_DX | Date | Date | Active | CMS updated |

FIG. 3G

Welcome admin | logout

ICD 10 CODES WITH 'NODX' MAPPING

ICD 10 CODES WITH 'NODX' AS PRIMARY CODE

| ICD10 CODE | CODE DESCRIPTION | CODE TYPE | MAPPING STATUS | MAPPING EFF. DATE | MAPPING TERM. DATE | COMMENTS |
|---|---|---|---|---|---|---|
| G432 | Status migrainosus | PCS | ACTIVE | Date | Date | CMS updated |
| T38906A | Underdosing of unspecified hormones and synthetic substitutes, initial encounter | PCS | ACTIVE | Date | Date | CMS updated |
| T38906D | Underdosing of unspecified hormones and synthetic substitutes, subsequent encounter | PCS | ACTIVE | Date | Date | CMS updated |
| T38906S | Underdosing of unspecified hormones and synthetic substitutes, sequela | PCS | ACTIVE | Date | Date | CMS updated |
| T38816A | Underdosing of anterior pituitary [adenohypophyseal] hormones, initial encounter | PCS | ACTIVE | Date | Date | CMS updated |
| T3881 6D | Underdosing of anterior pituitary [adenohypophyseal] hormones, subsequent encounter | PCS | ACTIVE | Date | Date | CMS updated |
| T3881 6S | Underdosing of anterior pituitary [adenohypophyseal] hormones, sequela | PCS | ACTIVE | Date | Date | CMS updated |
| T38896A | Underdosing of other hormones and synthetic substitutes, initial encounter | PCS | ACTIVE | Date | Date | CMS updated |

Home | Help

- ▲ ICD 10 MAPPINGS
- ▲ ICD 10 CLAIM MAPPINGS
- ▼ ICD 10 REPORTS
  - ICD 9 to ICD 10 Mappings
  - NODX Codes
  - User Change History
  - ICD 10 Change History-Dates
  - Active CMS Mappings
  - NODX - Change History
  - ICD 10 Effective Dates
  - ICD 10 Codes Status
- ▲ CLAIM REPORTS
- ▲ CONFIGURATION

FIG. 3H

ICD 10 USER CHANGE HISTORY

ICD 10 CHANGE HISTORY BY USER

Select the user name: [select here ▼] [select here]

[Search History]

CHANGE HISTORY FOR USER: KCRAJURI

| CODE TYPE | ICD 10 CODE | CODE DESCRIPTION | PRIMARY ICD 9 CODE | FIRST ADDITIONAL CODE | SECOND ADDITIONAL CODE | THIRD ADDITIONAL CODE | FOURTH ADDITIONAL CODE | MAPPING STATUS | MAPPING EFF DATE | COMMENTS |
|---|---|---|---|---|---|---|---|---|---|---|
| CMS | A000 | Cholera due to Vibrio cholerae 01, biovar cholerae | 0010 | N/A | N/A | N/A | N/A | ACTIVE | Date | CMS updated |
| CMS | A009 | Cholera, unspecified | 0009 | N/A | N/A | N/A | N/A | ACTIVE | Date | CMS updated |
| ABCBS | A000 | Cholera due to Vibrio cholerae 01, biovar cholerae | 0110 | N/A | N/A | N/A | N/A | LOADED | Date | USER updated |
| ABCBS | A000 | Cholera due to Vibrio cholerae 01, biovar cholerae | 9999 | N/A | N/A | N/A | N/A | LOADED | Date | USER MAPPING |
| ABCBS | T50B96A | Underdosing of other viral vaccines, initial encounter | 0019 | N/A | N/A | N/A | N/A | LOADED | Date |  |

Home | Help

- ICD 10 MAPPINGS
- ICD 10 CLAIM MAPPINGS
- ICD 10 REPORTS
  - ICD 9 to ICD 10 Mappings
  - NODX Codes
  - User Change History
  - ICD 10 Change History-Dates
  - Active CMS Mappings
  - NODX - Change History
  - ICD 10 Effective Dates
  - ICD 10 Codes Status
- CLAIM REPORTS
- CONFIGURATION Welcome admin logout

Home | Help

- ICD 10 MAPPINGS
- ICD 10 CLAIM MAPPINGS
- ICD 10 REPORTS
  - ICD 9 to ICD 10 Mappings
  - NODX Codes
  - User Change History
  - ICD 10 Change History - Dates
  - Active CMS Mappings
  - NODX - Change History
  - ICD 10 Effective Dates
  - ICD 10 Codes Status
- CLAIM REPORTS
- CONFIGURATION Welcome admin| logout

ACTIVE CMS MAPPINGS

ACTIVE CMS MAPPINGS OF ICD 10 CODES

| CODE TYPE | ICD 10 CODE | CODE DESCRIPTION | PRIMARY ICD 9 CODE | FIRST ADDITIONAL CODE | SECOND ADDITIONAL CODE | THIRD ADDITIONAL CODE | FOURTH ADDITIONAL CODE | MAPPING STATUS | MAPPING EFF DATE | COMMENTS |
|---|---|---|---|---|---|---|---|---|---|---|
| CMS | A043 | Enterohemorrhagic Escherichia coli infection | 00804 | N/A | N/A | N/A | N/A | ACTIVE | | CMS updated |
| CMS | A044 | Other intestinal Escherichia coli infections | 00800 | N/A | N/A | N/A | N/A | ACTIVE | | CMS updated |
| CMS | A045 | Campylobacter enteritis | 00843 | N/A | N/A | N/A | N/A | ACTIVE | | CMS updated |
| CMS | A046 | Enteritis due to Yersinia enterolitica | 00844 | N/A | N/A | N/A | N/A | ACTIVE | | CMS updated |
| CMS | A039 | Shigellosis, unspecified | 0048 | N/A | N/A | N/A | N/A | ACTIVE | | CMS updated |
| CMS | A047 | Enterocolitis due to Clostridium difficile | 00845 | N/A | N/A | N/A | N/A | ACTIVE | | CMS updated |
| CMS | A048 | Other specified bacterial intestinal infections | 00849 | N/A | N/A | N/A | N/A | ACTIVE | | CMS updated |
| CMS | A050 | Foodborne staphylococcal intoxication | 0050 | N/A | N/A | N/A | N/A | ACTIVE | | CMS updated |

FIG. 3L

Home | Help                                                                                                        Welcome admin logout

ICD 10 MAPPINGS
ICD 10 CLAIM MAPPINGS
ICD 10 REPORTS
  ICD 9 to ICD 10 Mappings
  NODX Codes
  User Change History
  ICD 10 Change History-
  Dates
  Active CMS Mappings
  NODX - Change History
  ICD 10 Effective Dates
  ICD 10 Codes Status
CLAIM REPORTS
CONFIGURATION

ICD 10 CHANGE HISTORY FOR NODX

ICD 10 NODX CHANGE HISTORY

| CODE TYPE | ICD 10 CODE | CODE DESCRIPTION | PRIMARY ICD 9 CODE | FIRST ADDITIONAL CODE | SECOND ADDITIONAL CODE | THIRD ADDITIONAL CODE | FOURTH ADDITIONAL CODE | MAPPING STATUS | MAPPING EFF. DATE | MAPPING CREATE ID | COMMENTS |
|---|---|---|---|---|---|---|---|---|---|---|---|
| CMS | T50A96A | Underdosing of other bacterial vaccines, initial encounter | NODX | N/A | N/A | N/A | N/A | ACTIVE | Date | | CMS updated |
| ABCBS | T50A96A | Underdosing of other bacterial vaccines, initial encounter | 73068 | N/A | N/A | N/A | N/A | LOADED | Date | | USER updated |
| CMS | T50B16A | Underdosing of smallpox vaccines, initial encounter | NODX | BONE INFECT NEC-OTH SITE | N/A | N/A | N/A | ACTIVE | Date | | CMS updated |
| ABCBS | T50B16A | Underdosing of smallpox vaccines, initial encounter | 70724 | N/A | N/A | N/A | N/A | LOADED | Date | | USER updated |
| CMS | T50B96A | Underdosing of other viral vaccines, initial encounter | NODX | N/A | N/A | N/A | N/A | ACTIVE | Date | | CMS updated |
| ABCBS | T50B96A | Underdosing of other viral vaccines, initial encounter | 0019 | N/A | N/A | N/A | N/A | LOADED | Date | | |
| CMS | T50B96A | Underdosing of other viral vaccines, initial encounter | NODX | N/A | N/A | N/A | N/A | ACTIVE | Date | | CMS updated |

Home | Help

- ICD 10 MAPPINGS
- ICD 10 CLAIM MAPPINGS
- ICD 10 REPORTS
- CLAIM REPORTS
  - Mapped Claims - Dates
  - Mapped Claims - Files
  - Claims with NODX - Files
  - Claims with NODX - Dates
  - Claims with Invalid ICD 10 - Dates
  - Claims with Invalid ICD 10 - Files
  - ICD 10 and ICD9 Claims - Dates
  - ICD 10 and ICD9 Claims - Files
  - ICD 10 Code in Claims - Files
  - ICD 10 Codes in Claims - LOB's
- CONFIGURATION

ICD 10 AND ICD 9 CODE STATISTICS FOR LOB'S

| SI No. | LOB | ICD 10 CLAIM COUNT | ICD 9 CLAIM COUNT | TOTAL FILES | 3D PIE CHART | 3D BAR CHART | XY CHART |
|---|---|---|---|---|---|---|---|
| 1 | BCBS | 49 | 9 | 14 | ⊙ | ▯▯ | xy |
| 2 | BAAA | 45 | 5 | 1 | ⊙ | ▯▯ | xy |
| 3 | HA | 14 | 3 | 2 | ⊙ | ▯▯ | xy |

Welcome admin | logout

METHOD AND SYSTEM FOR HEALTH CARE CODING TRANSITION AND IMPLEMENTATION

RELATED APPLICATIONS

This application claims priority to U.S. Provisional Application No. 61/202,364 titled "Method and System for Health Care Coding Transition and Implementation" filed Feb. 23, 2009, which is incorporated by reference herein in its entirety.

BACKGROUND OF THE INVENTION

1. Field of the Invention

Aspects of the present invention relate to the field of automated and other types of transitioning among health coding systems, nomenclatures, and transaction sets and implementation of such coding systems, nomenclatures, transaction sets, and other features.

2. Background of the Technology

In the related art, health care providers and/or health care plans may utilize a number of different computerized or other types of systems for management and tracking of the data involved in the health care payment process. In the United States, around 1500 health plans are estimated as being available for all health care payment entities nationwide. Although, many of these plans operate a vendor supply system, some level of customization may also be provided and, as a result, thousands of variations may be involved.

There is an unmet need in the art for methods and systems for implementing coding, nomenclature, and transaction set changes, among others, including coding changes for widespread use in the health care industry. There is a further unmet need in the art for methods and systems for assisting affected parties with tracking and implementing coding, nomenclature, and transaction set changes, among others.

SUMMARY OF THE INVENTION

Aspects of the present invention relate to methods and systems for implementing coding, nomenclature, and transaction set changes, among others, including coding changes for widespread use in the health care industry, as well as methods and systems for assisting affected parties with tracking and implementing coding, nomenclature, and transaction set changes, among others.

In accordance with illustrative aspects of the present invention, methods and systems involving three or more components may address the above, as well as other problems with coding and/or nomenclature change implementations. These components may include: 1) trading partner transaction processing and health plan benefit administration with contemporaneously used coding nomenclatures, for both local business and national business; 2) various health care industry constituents (e.g., employers; members; providers; regulatory authorities, both federal and state; and certification agencies) reporting, longitudinal analytics, and informatics within contemporaneously used coding nomenclatures (for both local and national business); and 3) business process relationships with statistically valid updates, including, for example, revalidation, recalibration, and/or fundamental reconstruction of business processes utilizing new coding nomenclatures.

Additional advantages and novel features of aspects of the invention will be set forth in part in the description that follows, and in part will become more apparent to those skilled in the art upon examination of the following or upon learning by practice of the invention.

BRIEF DESCRIPTION OF THE FIGURES

In the drawings:

FIGS. 2A-2C illustrates an exemplary representative flowchart for normalizing data, in accordance with aspects of the present invention;

DETAILED DESCRIPTION

Figure 1:
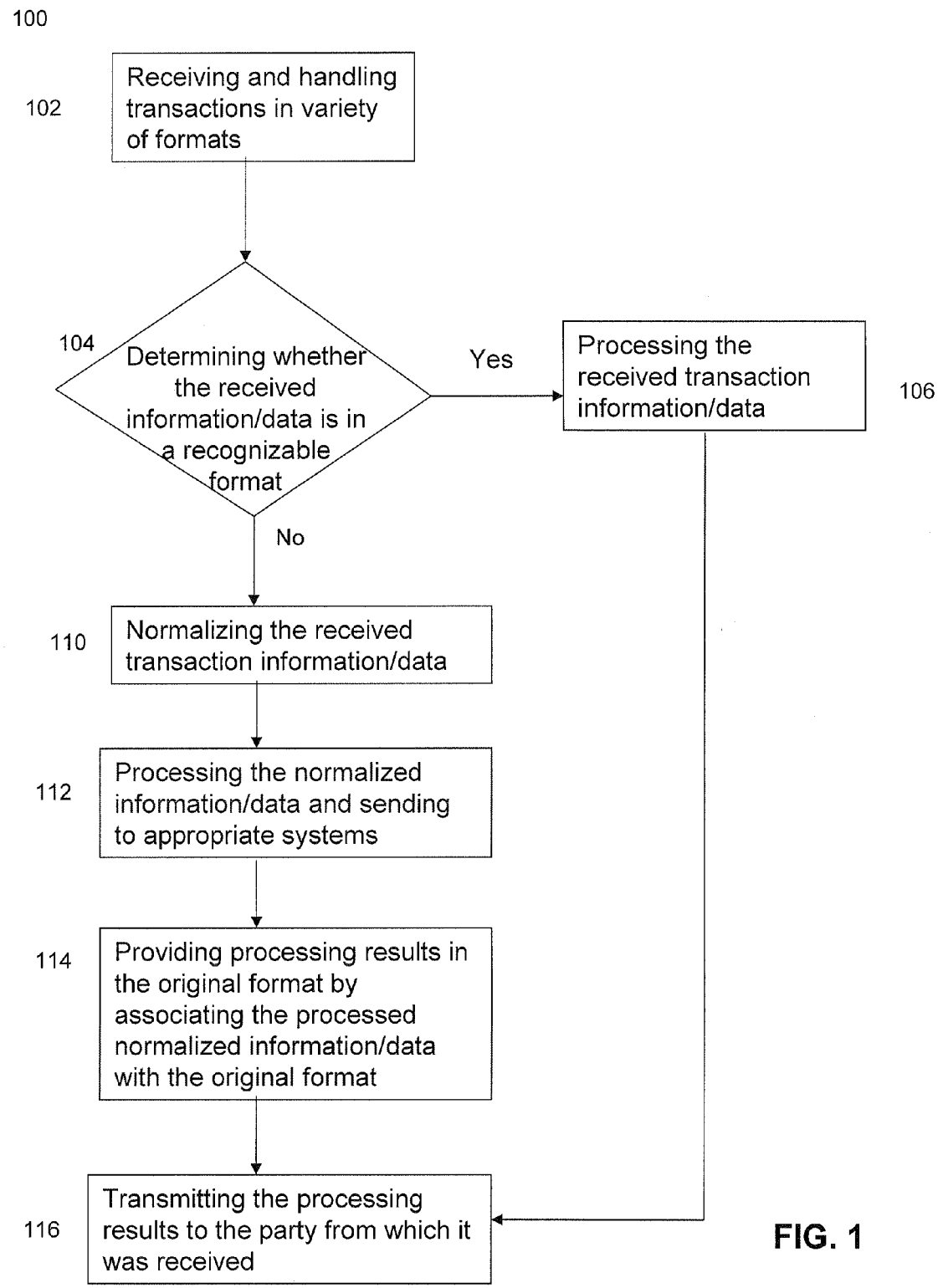
FIG. 1 presents an exemplary representative flowchart of an exemplary processing procedure for normalizing data, in accordance with aspects of the present invention.

Aspects of the present invention relate to methods and systems for implementing coding, nomenclature, and transaction set changes, among others, including coding changes for widespread use in the health care industry, as well as methods and systems for assisting affected parties with tracking and implementing coding, nomenclature, and transaction set changes, among others.

One exemplary aspect illustrating applicability of the present invention relates to implementation by the U.S. Office of Health and Human Services (HHS) of International Classification of Diseases (ICD) nomenclature for procedures and diagnoses from a current version (ICD0-9) to a new version (ICD-10), as well as implementation of the associated American National Standards Institute (ANSI) 5010 transaction set, from the current ANSI 4010 transaction set. Implementation of ANSI 5010 is mandated to be completed as mutually agreed upon among implementing parties by Jan. 1, 2012, prior to implementation of ICD-10. ICD-10 is to be implemented on Oct. 1, 2013.

The ICD and ANSI systems provide for coding (e.g., using a set of numeric or alphanumeric codes) and a set of health care related activities (e.g., health problems and procedures) that are used for various health care purposes, such as when tracking patient health care-related expenses and payment and/or reimbursement under health care insurance plans for these expenses.

One problem with the scheduled implementation of ANSI 5010 and ICD-10 is the lack of awareness of the mandated implementation. Among other things, implementation of ICD-10 and ANSI 5010 is expected to produce major problems for the affected parties, due to the massive scale of the changes and the current lack of planning and accounting for these changes when they are slated to occur. Further, upon implementation of ICD-10 and ANSI 5010, some degree of data uncertainty may occur for some period, until full implementation is completed (also referred to interchangeably herein as a period of "data fog").

Both the data fog and the implementation problems relating to these codes/nomenclature could have major financial consequences for the health care industry, such as delay in payments due to improper or incomplete implementation.

Understanding the scope of the transition from ICD-9 to ICD-10 and the associated transition from ANSI 4010 to ANSI 5010 as an illustrative example will now be provided so as to clarify some exemplary aspects of the present invention. ICD-9 has been utilized in the health care industry for approximately 30 years, so this system is well entrenched in the industry. Virtually all of the industry's business processes (e.g., on the provider side), clinical systems and clinical processes, associated electronic and other health records, practice management systems used to run various businesses within the industry, the coder industry that is used to generated claims for billings, activities, services rendered, and communications (e.g., communication of laboratory results, radiology results, and virtually any other type of medical services) are communicated based upon the ICD-9 nomenclature. Thus, for example, the "back and forth" between the health care service providers (e.g., doctors) and health plan providers (e.g., insurance companies) for services provided (including both diagnoses and services/procedures provided) and payment to be made occurs using the ICD-9 nomenclature.

Among other things, the ICD-9 structure drives benefit packages, and coverage of services is mostly determined using the ICD-9 nomenclature. Specifically, coverage information may include, for example, which services are covered, how the covered services will be reimbursed, what exclusions might exist, and what other provisions relating to the services may also be covered. Some or all of these factors are linked to the ICD-9 coding structures and procedure codes, which are used throughout the health care industry. The logic of these systems is used to drive administration of health plans, and the particular health care plan and premium likewise depend on the combination of ICD-9 based nomenclature coverage involved in that plan.

The depth of ICD-9's use and impact on the health care industry may further be illustrated by the fact that: approximately 11,000 diagnosis codes and about 13,000 procedure codes are included in ICD-9 (a total of about 24,000 codes).

Further, understanding the relationship between the ICD system and the Healthcare Insurance Portability and Accountability Act (HIPAA) is also important to understanding the impact of changes in the ICD system. HIPAA generally governs communications between the provider community and health plans, among other factors. One type of transaction involved is referred to as an "eligibility query," in which a provider may electronically or otherwise send a transaction in a standard HIPAA format to a health plan to determine eligibility for coverage, type of coverage, etc. An electronic response, for example, is then sent back by the health plan regarding coverage, scope of coverage, accumulations towards maximums, etc. The basis for these communications is in the existing ICD-9 structure.

Once coverage is confirmed, the provider may see the patient and provide services, such as diagnosis and treatment. Services may also implicate various other factors, such as office setting versus hospital setting, in-patient versus outpatient, etc.

Subsequent to completion of the visit for the patient, information work processes may be used to generate a claim (e.g., through a practice management system or hospital admission/discharge system), to summarize activities provided (e.g., diagnosis and procedures) and related charges, which are incorporated into a claim transaction under HIPAA. Typically, such claim transactions are 90% or more in electronic format industry-wide. These transactions may be communicated directly to a health plan or via a clearinghouse, for example. The basis of all this information is the ICD-9 coding nomenclature.

In contrast to ICD-9, which, as indicated above, involves about 24,000 codes relating to transactions, ICD-10, when implemented, will provide for about 155,000 codes. Within the coding structures for ICD-9 are "chapters," which have an organizational design (although no embedded logic is contained in the codes themselves).

The ICD-10 coding methodology will involve implementation of new transaction formatting. Under ICD-9, transactions currently occur in ANSI 4010 A-1 format (the current format version for health care transactions). As a first step in moving to the ICD-10 coding methodology, a format change must be made from ANSI 4010 A1 to ANSI 5010. Approximately 835 changes are involved in making this format change, most of which are relatively minor in nature. Nevertheless, technically, a format change must occur for these minor changes.

In addition to these mostly minor format changes, a number of major changes will accompany the ANSI 5010 implementation, in preparation for the shift to ICD-10 coding nomenclature. One potentially significant change is in the size of data coding. For diagnosis codes, a change will occur from five digit, numeric only coding under ICD-9, to seven digit, alphanumeric coding under ICD-10. This alphanumeric coding under ICD-10 will also include an embedded logic within the coding structure that does not exist in the ICD-9 structure. Similarly, for procedure codes, which are typically two to four numeric digits under ICD-9, coding will move to seven alphanumeric digits with embedded coding.

These ANSI coding changes are necessary as an initial step prior to implementation of ICD-10. These changes must take place for each provider and each health plan. One problem that will necessarily occur with this change is a differing pace of adoption across providers and plans.

Other problems with the coding change between ANSI 4010 A-1 and ANSI 5010 include the fact that some parts of the human body (e.g., for patients being treated) and some of the services involved have been moved to different chapters, and some redefinition of aspects of the coding and reporting mechanism under ICD-10 have occurred. Each of these changes may have major effects on how computerized and/or other automated systems handle the coding.

These differences may be illustrated by some examples for ICD-9 and ICD-10 coding. Under ICD-9, not all 24,000 codes may have been included in computer code. Instead, for example, ranges may have been provided for a particular service, and a number of codes, for example, may have been included in that range. Adjudication of the services occurs to determine how to proceed under the plan using ranges and codes. However, under ICD-10, for example, some of the codes in these ranges within ICD-9 may have been moved to a different chapter, a larger range of codes may be used, and benefits may differ in chapters where some codes have been moved. As a result, use of the ANSI 5010 coding with ICD-10 may produce errors in benefits payments, and it may not be possible to simply map some changes resulting from the code change between the ANSI 4010 A-1 coding and the ANSI 5010 coding.

In addition to direct coding change issues, other computer programming and/or other interpretive analysis of existing systems may need to occur with ICD-10 implementation, such as for fraud and abuse or utilization edits. For example, when a patient is coded for a hysterectomy, existing ICD-9 systems may determine (e.g., in programming) that the service is inappropriate if the patient is male. Similarly, certain ranges of services may be matched as appropriate for certain diagnoses. This coding interpretation of these activities may or may not be easily transferable using ICD 10 after the change from ICD 9.

Another example of ICD-9 related existing programming or other interpretive analysis that may need to be addressed is in response to services falling outside of a given range. For example, in some cases, a "soft suspend" occurs when a treatment falls outside of a range, requiring review of the treatment by a human claims examiner. If a claims examiner cannot make such determination, a physician or nurse must review the claim. In other cases, if the treatment is determined to be inappropriate for the diagnosis, the claim is simply denied, which is referred to as a "hard denial." All of these functions are based on existing ICD 9 coding infrastructure.

As discussed in more detail below, some changes may not be simple to implement and/or may not be appropriate for implementation once the change to ICD-10 occurs. In making these determinations, a process interchangeably referred to herein as "revalidation" may be necessary. With revalidation, relationships among ICD-9 coding related aspects may need to be reevaluated under ICD-10 to determine if the relationships remain valid. For example, if a particular procedure under ICD-9 has been determined to appropriately occur every two years, diagnosis for the procedure in less than two years may previously have been determined to require a soft suspend, for example. However, under ICD-10, additional granularity may allow the procedure to be performed, because additional details have been captured. For example, under ICD-10, the procedure may have been performed on a right arm less than two years ago, but not on a left arm, and coding information may capture this granularity. As a result, under ICD-10, a soft suspend may be inappropriate.

Building up the statistical or other information to support the new knowledge base for this type of logic development under ICD-10, interchangeably also referred to herein as "recalibrating," may be necessary. These changes may result in including, excluding, and/or adding new logic coding.

Further, the provider community must be retrained for the implementation of ICD-10, including potentially every healthcare professional, including doctors and nurses, among others. The implementation is likely to require the gathering of much more information at the point of service than previously required for ICD-9. For example, under ICD-9, if a child under a plan is injured during a sporting event, requiring a stitch on the head, a single code would cover this procedure (e.g., laceration on head; sewing laceration; treatment with antiseptic). However, under ICD-10, 29 codes could be utilized for defining this service, and additional information may be needed to determine which code to use. For example, the information may include specifics on what caused the gash, such as impact by a hockey puck, hockey stick, football, or football cleat.

While this information may be communicated during treatment within the existing ICD-9 process, it typically may not be contained within the ICD-9 coding process. Further, recording this information will not result in any change in payment occurring. In addition, while ICD-10 will allow for indication of "otherwise unspecified" for certain information, in many cases, the selection of this indication will result in denial of payment, thereby forcing the practitioner to provide this information later, thereby delaying payment. The net result of some of these changes is that additional work, and hence increased expense, may be required for payment to occur, but no additional direct benefit (e.g., increased payments) may result for health care industry participants involved.

As a result, a disincentive will likely occur for implementation of ANSI 5010 and ICD-10, providing an implementation speed that will likely vary significantly across the health care industry, with varying amounts of implementation being simultaneously in place over a significant period of time (e.g., 5-7 years). Further, while implementation of ANSI 5010 may be by mutual agreement between two parties and implemented over time, with a final implementation target date specified, ICD-10, in contrast, is mandated to be implemented in a single step industry-wide on Oct. 1, 2013, a mandate that will likely be impossible to meet, especially given all the synchronization and cost issues involved.

A further complication likely to produce varying pace of implementation is that computerized and other systems involved will need to handle multiple ANSI standards and ICD code levels at the same time, in order to be able to translate and cross work with other platforms for which implementation is incomplete.

In accordance with illustrative aspects of the present invention, methods and systems involving three or more components may be used to address the above, as well as other problems with coding and/or nomenclature change implementations. These components may include: 1) trading partner transaction processing and health plan benefit administration with contemporaneously used coding nomenclatures for both local business and national business; 2) various health care industry constituents (e.g., employers; members; providers; regulatory authorities, both federal and state; and certification agencies) reporting, longitudinal analytics, and informatics within contemporaneously used coding nomenclatures (for both local and national business); and 3) business process relationships with statistically valid updates, including, for example, revalidation, recalibration, and/or fundamental reconstruction of business processes utilizing new coding nomenclatures.

These components, for example, may include software and/or other automated or other types of assistance with normalizing the negative effects of contemporaneous transactions among the iteratively implemented/de-implemented nomenclatures and transaction sets (as used interchangeably herein, normalizing refers to and/or otherwise accounts for various differences among implemented, partially implemented, or not yet implemented systems and/or features). In addition, these components may include features of recording, storing, and/or reporting the normalized data. Further, software and/or other automated or other types of features may be needed for recalibration/revalidation over time, as implementation is iteratively or otherwise completed and refined.

In the related art, providers and/or health care plans may utilize a number of different computerized or other systems for management and tracking of the data involved in the health care payment process. For example, within the Blue Cross system alone, 39 independent health plans are currently provided, and about 100 different claim systems operate within those plans. In the United States, around 1500 health plans, TPA's and HMO's are estimated as being available for all health care payment entities nationwide. While many of these plans operate a vendor supply system, some level of customization may also be provided. As a result, thousands of variations may be involved. However, the commonality for all of these plans currently is use of ICD-9 diagnosis and procedure coding structures.

Among the problems, therefore, that health plans and other entities encounter with such coding system changes during transitions among such systems, are the following: 1) the requirement to receive and accept a qualified transaction, regardless of the coding format that the health plan receiver is using at the time (e.g., if implemented on or ahead of schedule); 2) responding to the sender in the standard transaction set, which is the currently accepted nomenclature in practice by the government's definition of what HIPAA transactions should be in play at that time; and 3) maintaining benefit and transaction information for a member in a single location to ensure proper adjudication of health care benefits purchased, including proper tracking and other accounting of accumulated deductibles, co-insurance paid, and/or other benefits, etc.

In implementing this approach, aspects of the present invention relate to a number of exemplary feature groups for addressing the above and other problems with implementation of multiple coding systems and other similar problems. These feature groups may include (e.g., for ANSI 4010 to 5010 and ICD-9 to ICD-10 implementation, for example): 1) trading partner transaction processing and health plan benefit administration with two contemporaneously used ICD coding nomenclatures, for both local business and national business; 2) various health care industry constituents (e.g., employers; members; providers; regulatory authorities, both federal and state; and certification agencies) reporting, longitudinal analytics, and informatics within two contemporaneously used ICD coding nomenclatures (for both local and national business); and 3) business process relationships with statistically valid updates, including, for example, revalidation, recalibration, and/or fundamental reconstruction of business processes utilizing the new ICD-10 coding nomenclature.

Referring now to FIG. 1, aspects the present invention provide for normalizing, for example, various types of transactions occurring during the transition process, as illustrated by exemplary method 100. The method includes receiving and handling received transactions in a variety of coding formats and code implementations 102. For example, a user (e.g., a trading partner, a hospital, or a doctor's office, among others) may provide a variety of transactions in a variety of coding formats and code implementations to a computing system at, for example, a health plan provider (e.g., an insurance company). Transactions may include, for example, an eligibility query, or a claim transaction (e.g., summaries of activities provided and charges for the services provided), among other transactions. The coding formats and/or code implementations for the transaction may include, for example, ICD-9, ICD-10, ANSI 4010, and ANSI 5010, among others. Thus, the computing system at the health plan provider may, for example, receive a claim transaction using an ICD-10 coding format from a trading partner.

In addition, the method 100 includes determining whether the coding format for the received transaction is in a recognizable format 104. A recognizable format may be a coding format and/or code implementation for the received transaction that is similar to and/or the same as the coding format that the computing system is using. For example, if the computing system is operating an ICD-9 nomenclature and receives a transaction with an ICD-9 code, the computing system would recognize the ICD-9 transaction as the same and/or similar type of code used by the computing system. Therefore, the transaction using an ICD-9 coding format would be in a recognizable format. Alternatively, if the computing system receives a transaction operating with an ICD-10 nomenclature, the computing system may not recognize the ICD-10 coding format, and thus, the transaction would be in an unrecognizable format.

If the received information/data is in a recognizable format, the method includes processing the received transaction information/data 106. Processing the received transaction information/data may include, for example, processing an eligibility query, performing claims management (e.g., performing claim editing and/or review; performing utilization review editing and/or payment editing; and addressing fraud and abuse of claims), and storing information associated with the transaction, among other processing of the received transaction information/data. The processed information/data is transmitted to the party from which it was received 116.

If the received information/data is in an unrecognizable format the method includes normalizing the received transaction information/data 110. Normalizing the received transaction information/data may include transforming and/or translating the received transactions into a format recognizable by the computing system. For example, if the computing system is operating with an ICD-9 nomenclature and receives a transaction operating with an ICD-10 code, then the computing system, in accordance with one aspect of the present invention, may transform the ICD-10 transaction into an ICD-9 transaction (e.g., transforming the ICD-10 code into an ICD-9 code). The normalization process may be applied to a variety of codes and formats. Examples of normalizing algorithms are discussed below in regards to FIGS. 2A-2C.

The method 100 includes processing the normalized transaction information/data 112. As discussed above, processing the received transaction information/data may include, for example, processing an eligibility query, performing claims management (e.g., performing claim editing and/or review; performing utilization review editing and/or payment editing; and addressing fraud and abuse of claims), and storing information associated with the transaction, among other processing of the received transaction information/data 106. Placing the received transactions into a common nomenclature format for use internally, provides a degree of certainty in the validity of claim editing, allows utilization review editing and payment editing, and is of assistance in addressing fraud and abuse concerns for the benefit plan designs sold and administered, for example.

In addition, the method 100 includes providing the processing results in the original format by associating the processed normalized information/data with the original format 114, which may be accomplished by reversing the normalization process of the processed information/data. It should be appreciated that the computing system may use the same or different transformations and/or translations as those used in step 110 for reversing the normalization of the processed information/data. Alternatively, it should be appreciated that providing the processing results in the original format may be performed by locating the originally submitted code/format and inserting the originally submitted code/format automatically as the reverse normalization. Thus, the computing system, according to an aspect of the present invention, is capable of intelligently reversing the common nomenclature formatting for responding to the transaction initiator in the format that the initiator utilized (e.g., changing the ICD-9 code back to an ICD-10 code).

Further, the method includes transmitting the processing results to the party from which it was received 116. The processing results may include a response to an eligibility query (e.g., scope of coverage for an individual, accumulations towards maximums, etc.), or payment for services provided to a patient, among other processed information/data. The response to the transaction initiator may be in the format that the initiator utilized. This procedure may be particularly difficult to implement for some health plan providers, for example, that have multiple subprovider entities (e.g., regional plans). For example, implementation in this circumstance may require multiple normalization procedures in different regions to allow adjudication or other activity within different subprovider entities, which may have differing common nomenclature formats (e.g., because of differing rates of implementation of codes/nomenclatures).

Figure 2B:
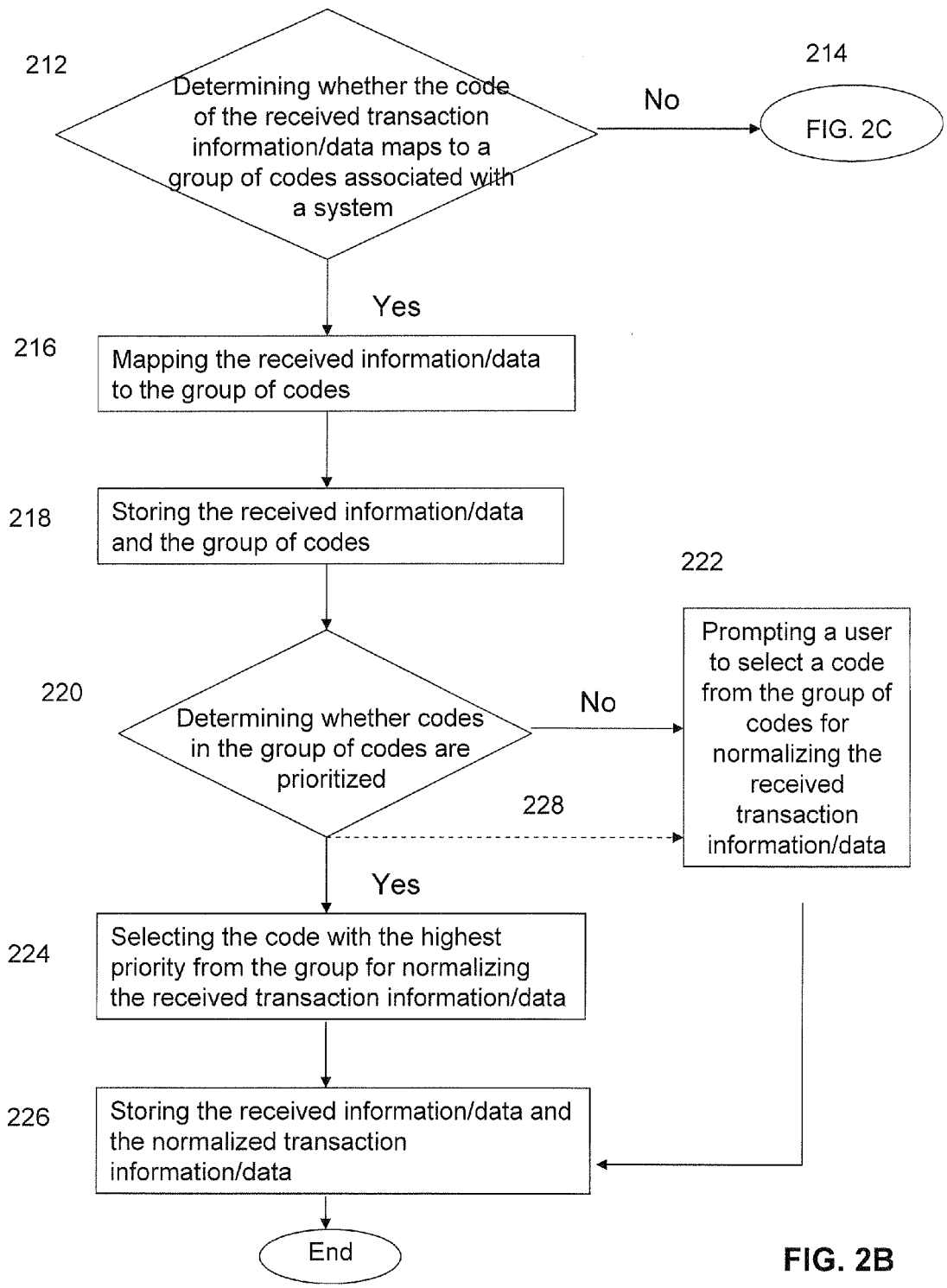
Figure 2C:
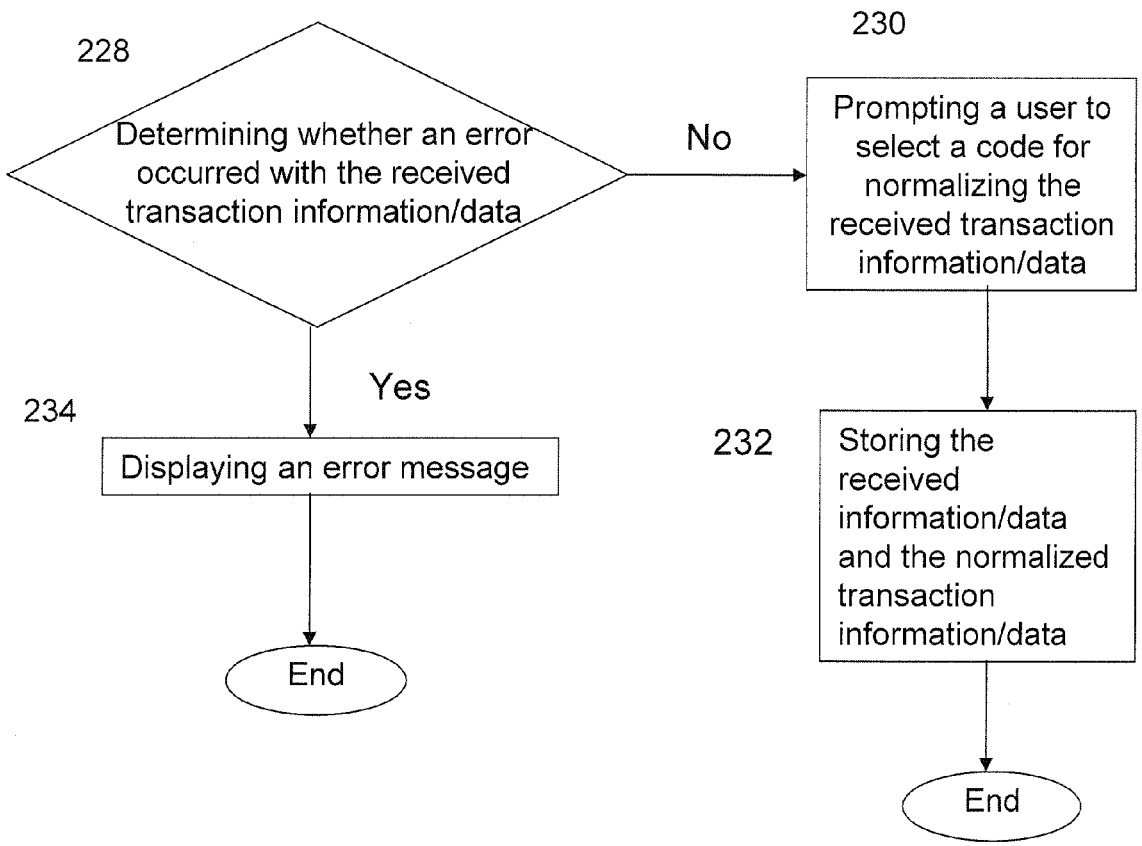

Turning now to FIGS. 2A-2C, a method 200 for normalizing data in accordance with aspects of the present invention is disclosed. The method includes receiving a transaction 202. As discussed above in regards to FIG. 1, the transactions may be in a variety of coding formats and code implementations.

Further, the method includes determining whether the coding format for the received transaction maps to a coding format associated with a system (e.g., a one-to-one mapping with the code format for the health provider's computing system) 204. For example, if the computing system is operating in an ICD-9 nomenclature and the received transaction includes an ICD-10 code, the computing system may determine whether the ICD-10 code for the received transaction maps to an ICD-9 code. In an aspect, an automated tool may be used for mapping the received transaction information data to a code associated with the system. The automated tool may include a data repository of mappings from one code implementation and/or coding format to a different code implementation and/or coding format. Examples of automated tools that may be used for mapping the coding formats include CMS (Center for Medicare and Medicaid Services) Reimbursement Mapping tool and GEM (General Equivalence Mapping) Analysis tool, among others. For example, the automated tool may search the data repository with the ICD-10 code for the received transaction information for determining whether a corresponding ICD-9 code is associated with the received ICD-10 code. In one aspect, the data repository of code mappings may be populated by a user adding and/or removing codes from the data repository, or from previous transactions. If the code for the received transaction information/data does map to a code format associated with a system, e.g., if the ICD-10 code corresponds to an ICD-9 code, the method includes mapping the received transaction information/data to the code associated with the system 208. For example, the computing system may map the ICD-10 code to the corresponding ICD-9 code. Thus, the received transaction information/data is now associated with both an ICD-10 code and a corresponding ICD-9 code.

Further, the method includes storing the received transaction information/data and the mapped transaction information/data 210. Storing the received transaction information/data with both the original code and the mapped code may be used for generating reports and performing analysis on the collected data. Examples of analysis and reporting are discussed below in relation to FIGS. 3O-3X.

If the code of the received transaction information/data does not map to a single code implementation associated with a system, continues to step 206, where the method continues with the flow diagram illustrated in FIG. 2B.

Turning now to FIG. 2B, the method may include determining whether the coding format for the received transaction information/data maps to a group of codes associated with a system 212. For example, the health provider's computing system may determine that the received transaction's ICD-10 code maps to a cluster of ICD-9 codes, e.g., one or more ICD-9 diagnosis codes or procedural codes that relate to the received ICD-10 code. It should be appreciated that the size of the group may be limited to a maximum number of codes that may be included in the group. For example, the size of the group may be limited to 5 codes. As discussed above, an automated tool may be used for mapping the received transaction information data to a group of codes associated with the system 204. The automated tool may include a data repository of mappings from one code implementations and/or coding formats to a group of different code implementations and/or coding formats.

If the code for the received transaction information/data does map to a group of code implementations, the process maps the received transaction information/data to the group of codes 216. For example, the computing system may map the ICD-10 code to a corresponding group of ICD-9 codes. Thus, the received information/data transaction is now associated with both an ICD-10 code and a group of corresponding ICD-9 codes. Further, the method includes storing the received transaction information/data and the group of codes the transaction code maps to 218. Storing the received transaction information/data with both the original code and the mapped group of codes may be used for generating reports and performing analysis on the collected data. Examples of analysis and reporting are discussed in relation to FIGS. 3O-3X.

In addition, the method includes determining whether the provided groups of codes are prioritized 220. For example, the computing system may determine whether the group of codes has a priority order, e.g., primary codes and secondary codes, a number ranking the codes descending from the highest ranked code to the lowest rank code, or may identify which codes are active or inactive, among other prioritization of the codes. If the groups of codes are prioritized, the method includes selecting the code with the highest priority from the group for normalizing the received transaction/information 224. For example, the computing system may select the code with the highest priority, e.g., the primary code or the code with the highest ranking, for normalizing the received transaction/information. Further, the method includes storing the received transaction information/data and the normalized transaction information (e.g., the code selected by the computing system for normalizing the transaction information/data) 226.

If the codes are not prioritized, the method includes prompting a user to select a code from the group of codes for normalizing the received transaction information/data 222. For example, a user may select a code from the group of codes, e.g., the group of ICD-9 codes, whose description is closest to the ICD-10 code for the received transaction. In addition, even if the codes are prioritized, the process may optionally follow to prompting a user at 222. Thus, the user may override the grouping of the codes and enter a different code for normalizing the code of the received transaction. Thus, the mapping may be customized for different organizations and/or users. Further, the method includes storing the received information/data and the normalized transaction information 226.

If the code of the received transaction information/data does not map to a group of code implementations associated with a system, the method continues with the flow diagram illustrated in FIG. 2C, at 214.

Turning now to FIG. 2C, the method may include determining whether an error occurred with the received transaction information/data 228. An error may include the situation when the received transaction information/data was improperly entered (e.g., the ICD-10 code or ICD-9 code did not include the proper length of characters and/or an improper character was included in the code), or when the code of received transaction information/data is an invalid code (e.g., the code does not exist), among other errors. If the computing system determines that an error occurred at submission, the method includes displaying an error message 234. For example, the computing system may display an error message to a user on a display indicating an error occurred with the submission. Capturing errors at submission helps prevent fraud and abuse of claims.

If the computing system does not determine that an error occurred at submission, the method includes prompting a user to select a code for normalizing the received transaction information/data 230. For example, the user may select an ICD-9 code that corresponds to the ICD-10 code of the received transaction. Further, the method includes storing the received information/data and the normalized transaction information/data 232. As discussed above and in more detail below, storing the received transaction information/data with both the original code and the mapped group of codes may be used for generating reports and performing analysis on the collected data.

Aspects of the present invention relate to supporting data collection (e.g., relating to performance and feedback) and reporting to, for example, a customer base, providers, various regulatory bodies at both the federal and state level that are involved in the health care system, and certification of other entities. For example, a customer (e.g., an employer buying a plan) may require reporting on all claims handled relative to a metric relating to that plan's implementation. This reporting is typically longitudinal in nature (e.g., covering a multiple year period), and reporting must be consistent, regardless of the level of implementation of coding/nomenclature of the reporting party (e.g., the health plan provider) and the level of implementation of coding/nomenclature of other actors in the health care system (e.g., service providers; other insurers). Reporting prior to implementation of a new coding/nomenclature must be consistent with reporting during partial implementation and with reporting following full implementation.

One aspect of the invention includes setting up data bases or other data repositories and reporting methodologies that are equivalent to historical reporting approaches.

Figure 3A:
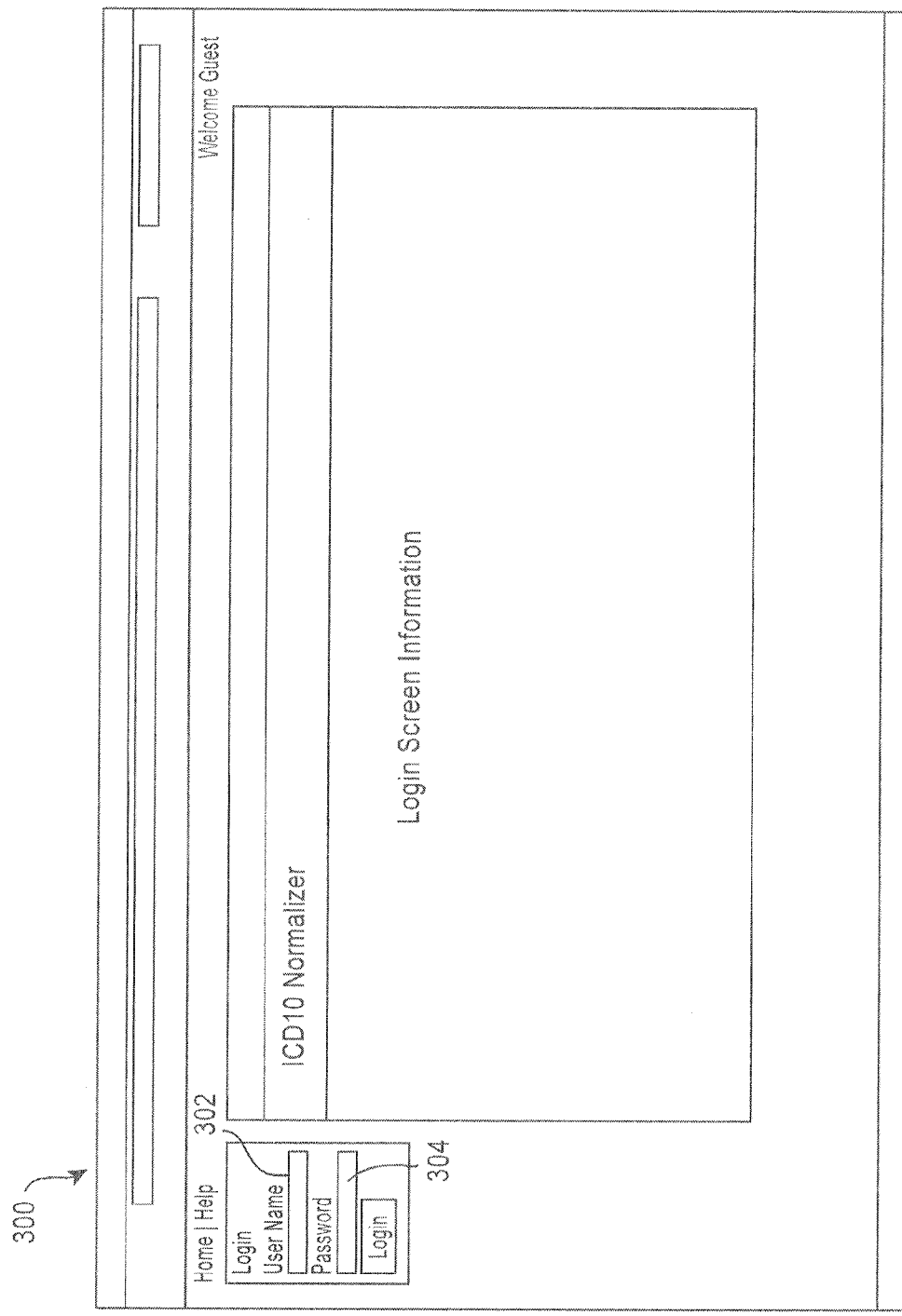
FIGS. 3A-3Z present exemplary Graphic User Interface (GUI) screens, in accordance with aspects of the present invention.
Figure 3C:
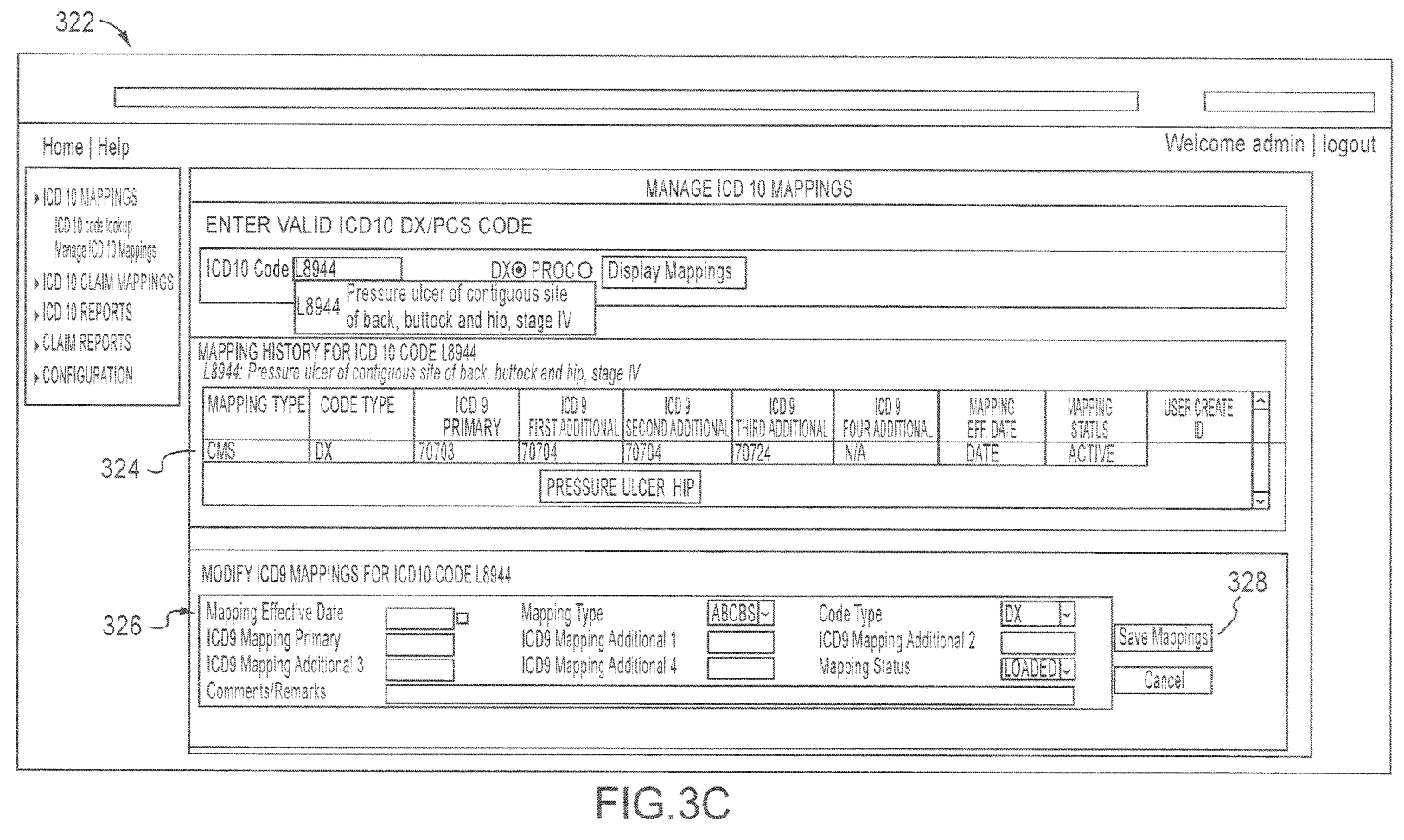
Figure 3D:
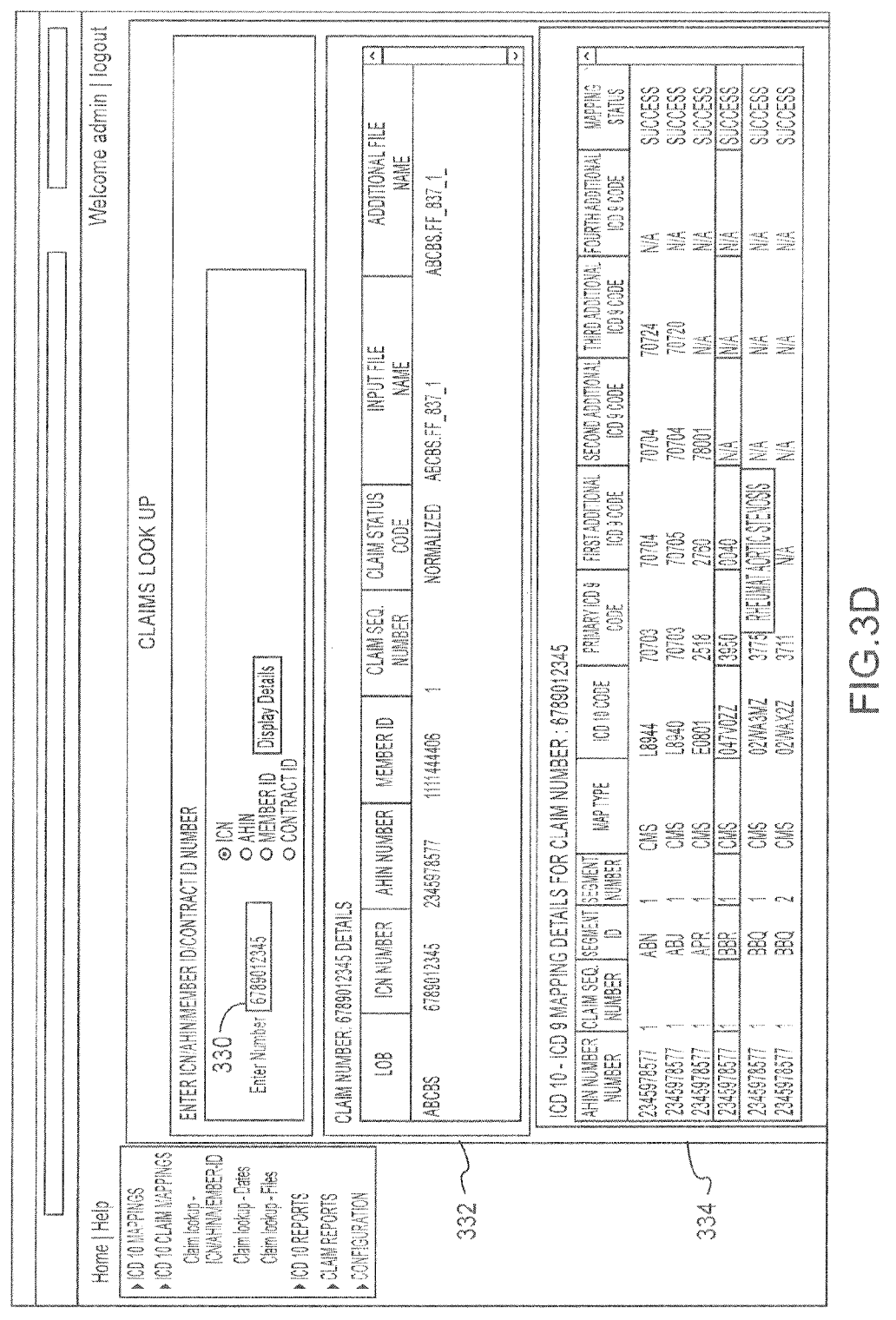
Figure 3J:
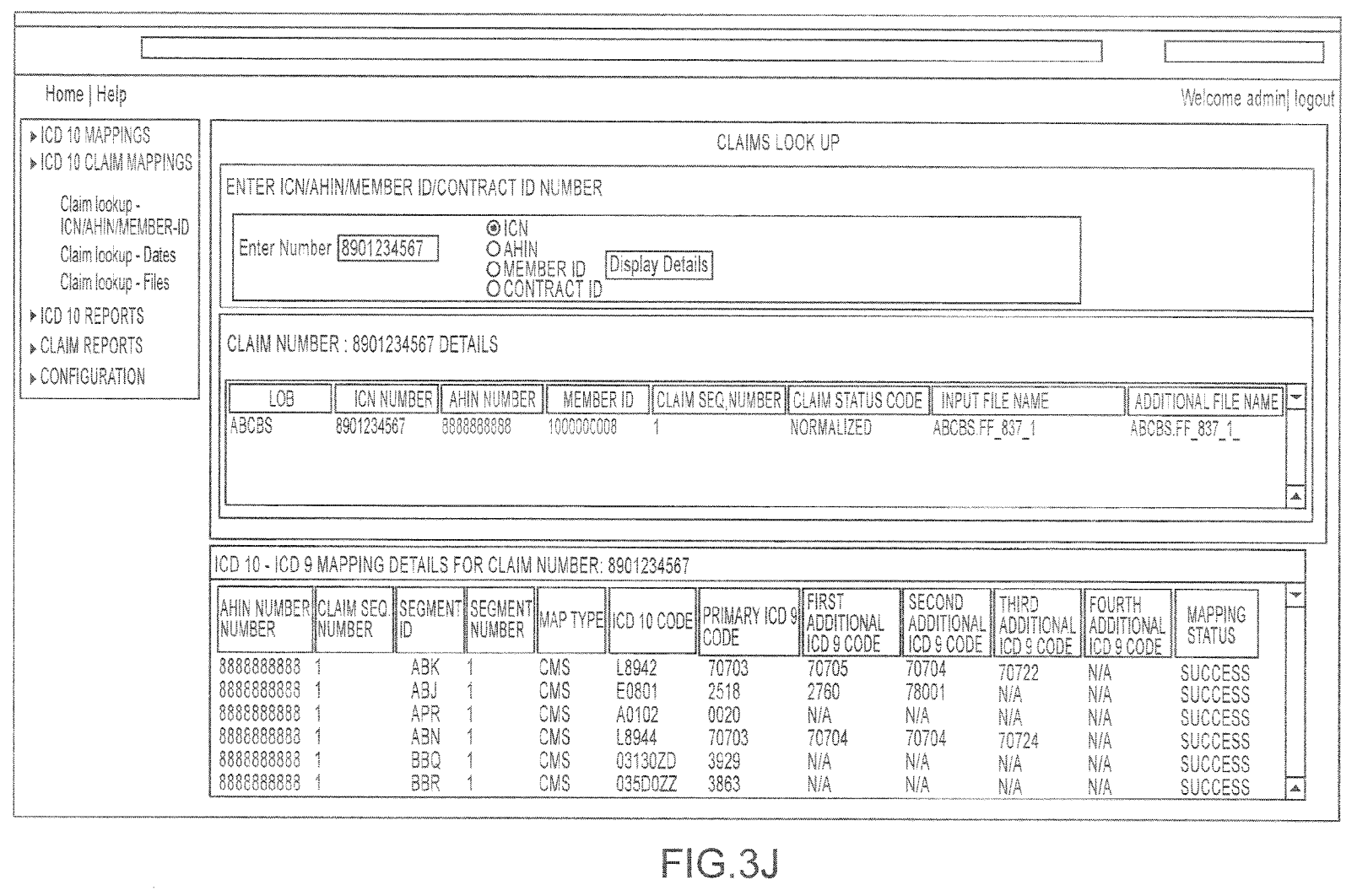
Figure 3K:
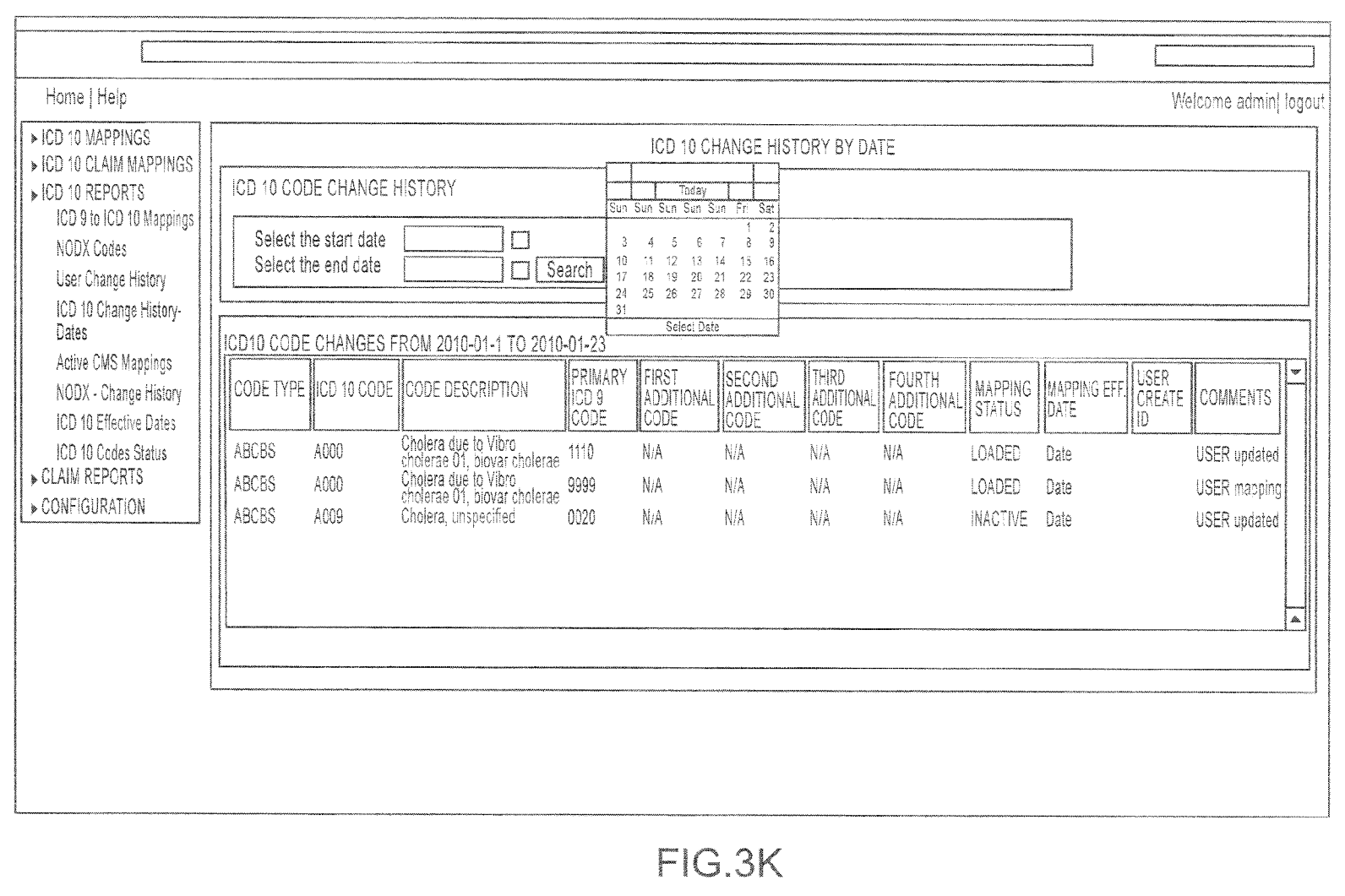
Figure 3N:
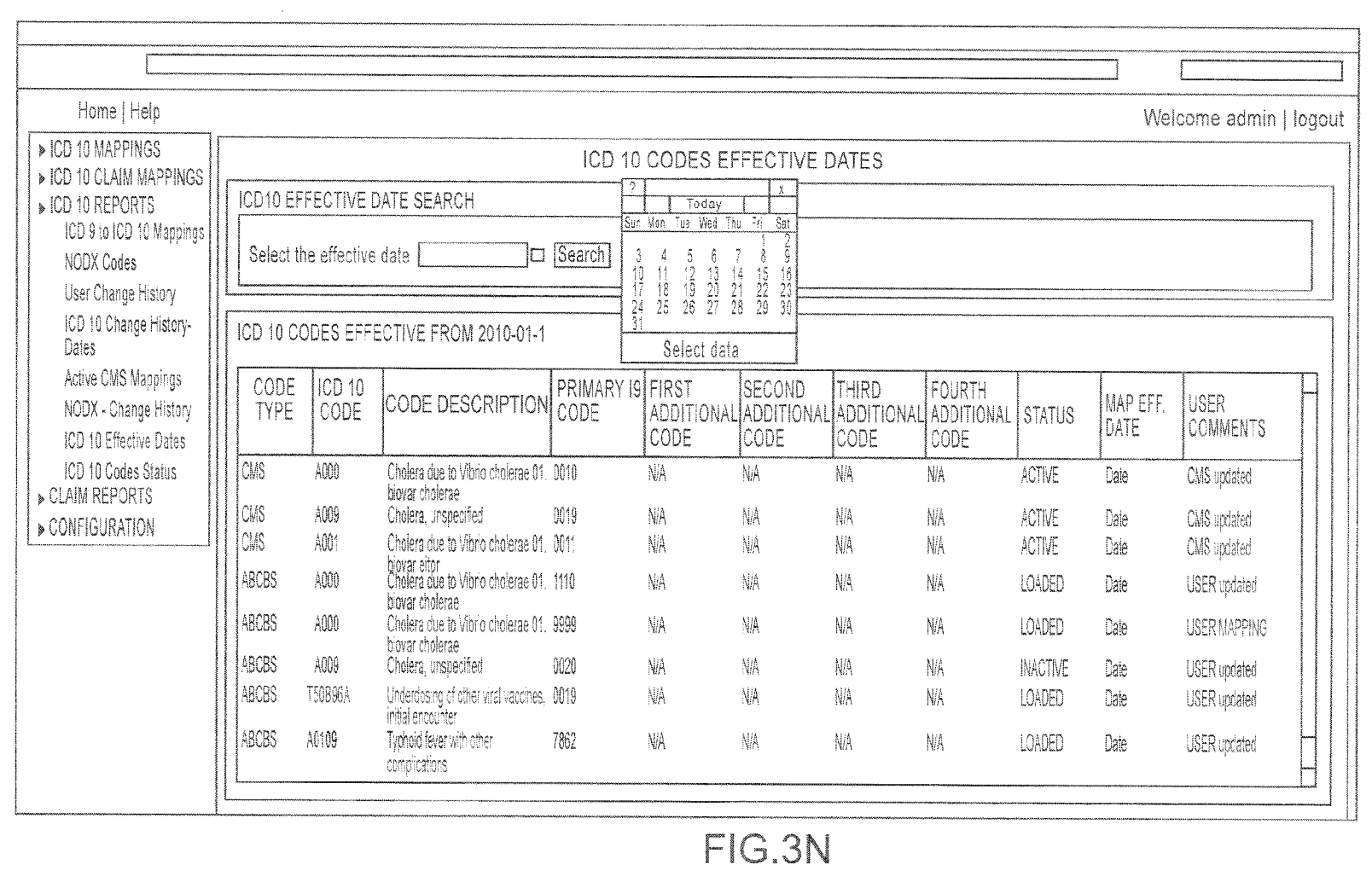
Figure 30:
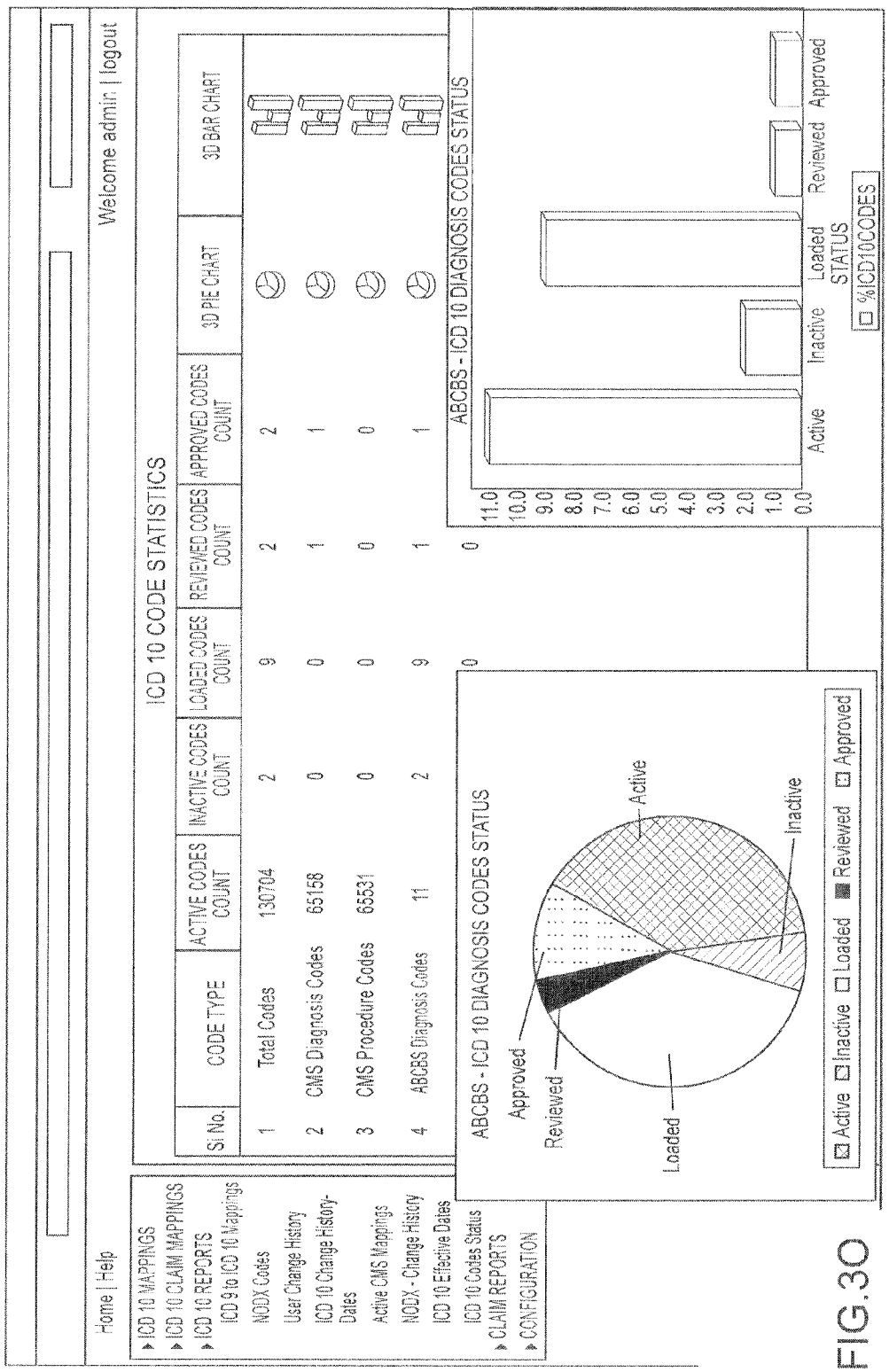
Figure 3P:
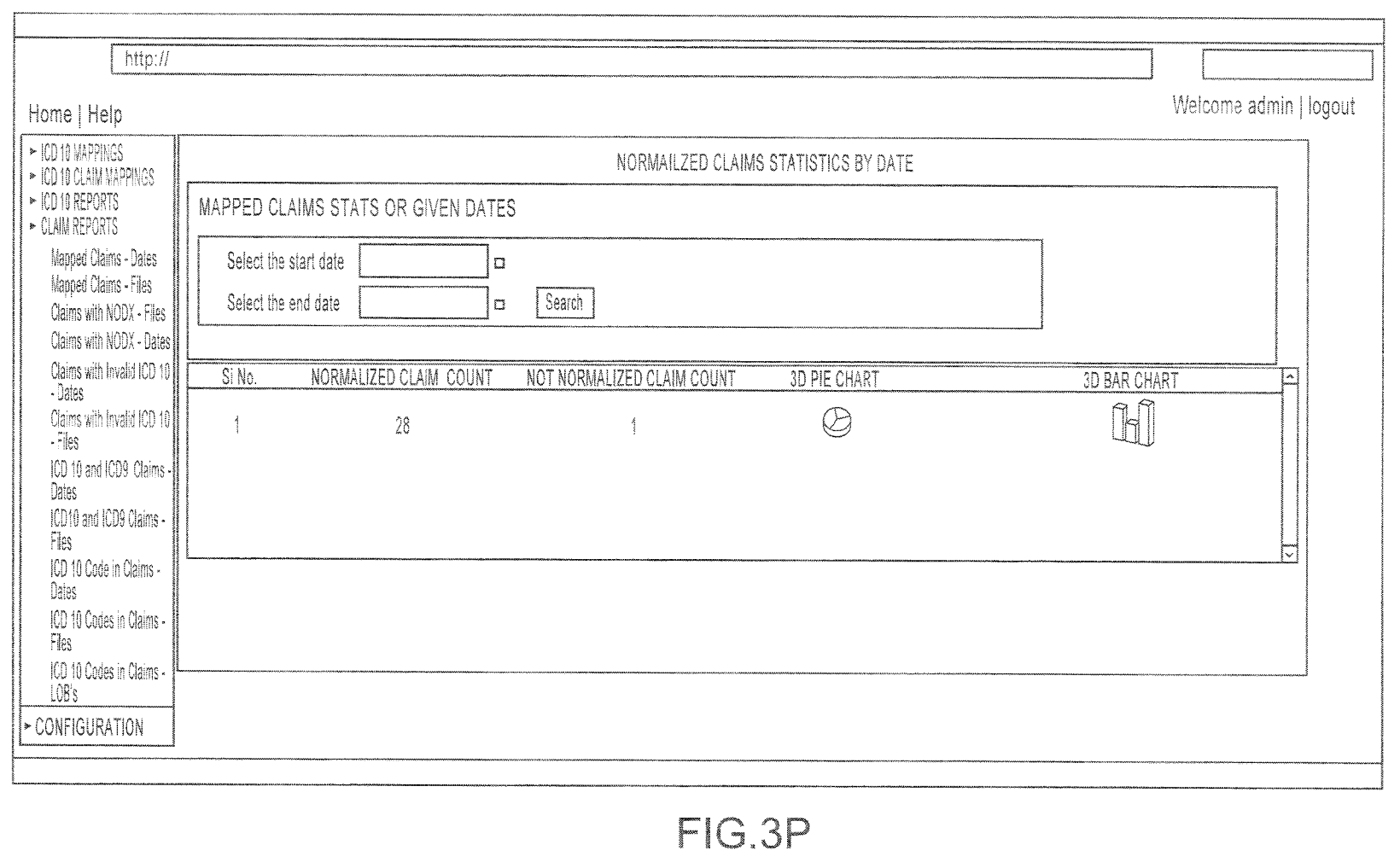
Figure 3Q:
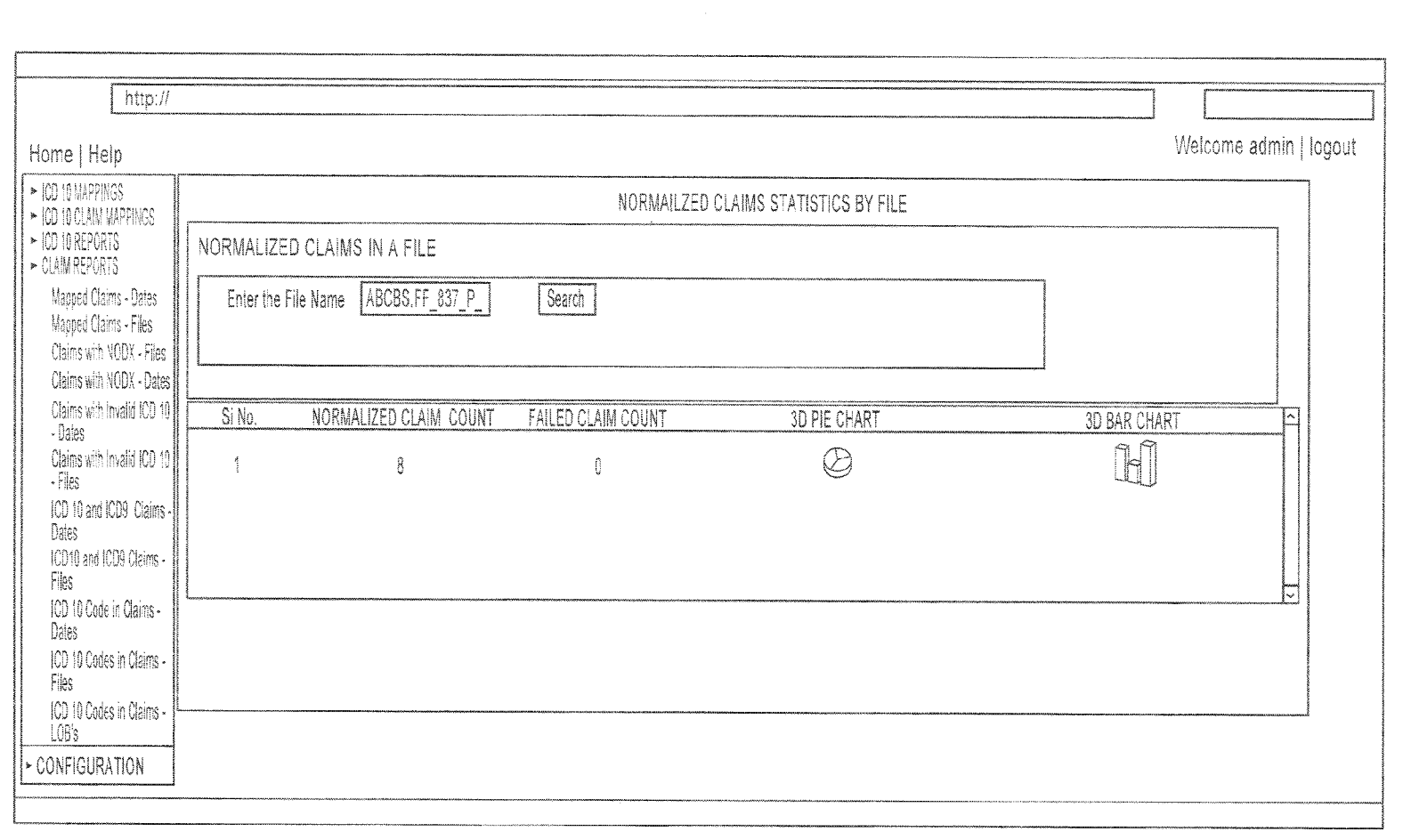
Figure 3R:
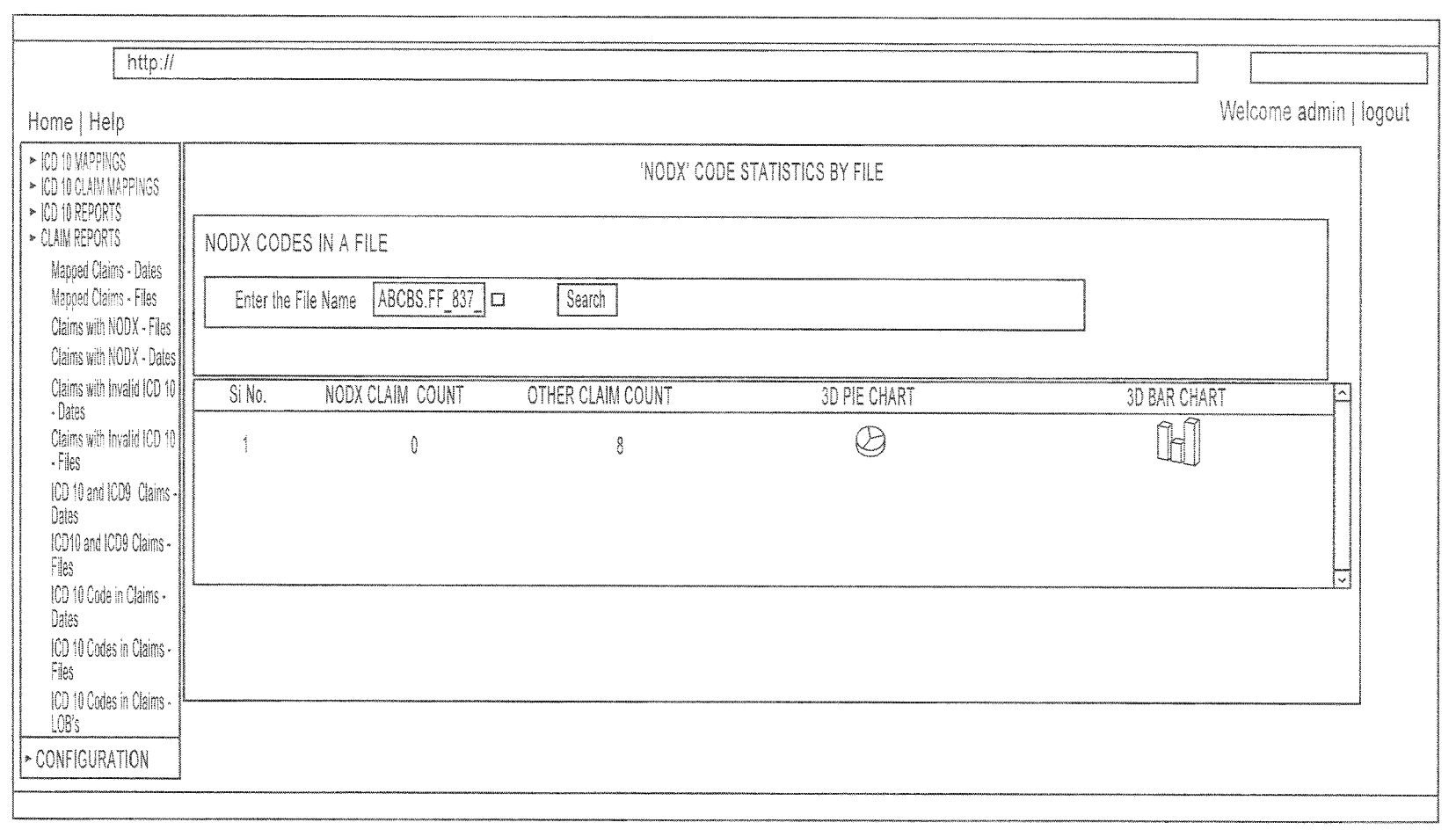
Figure 3S:
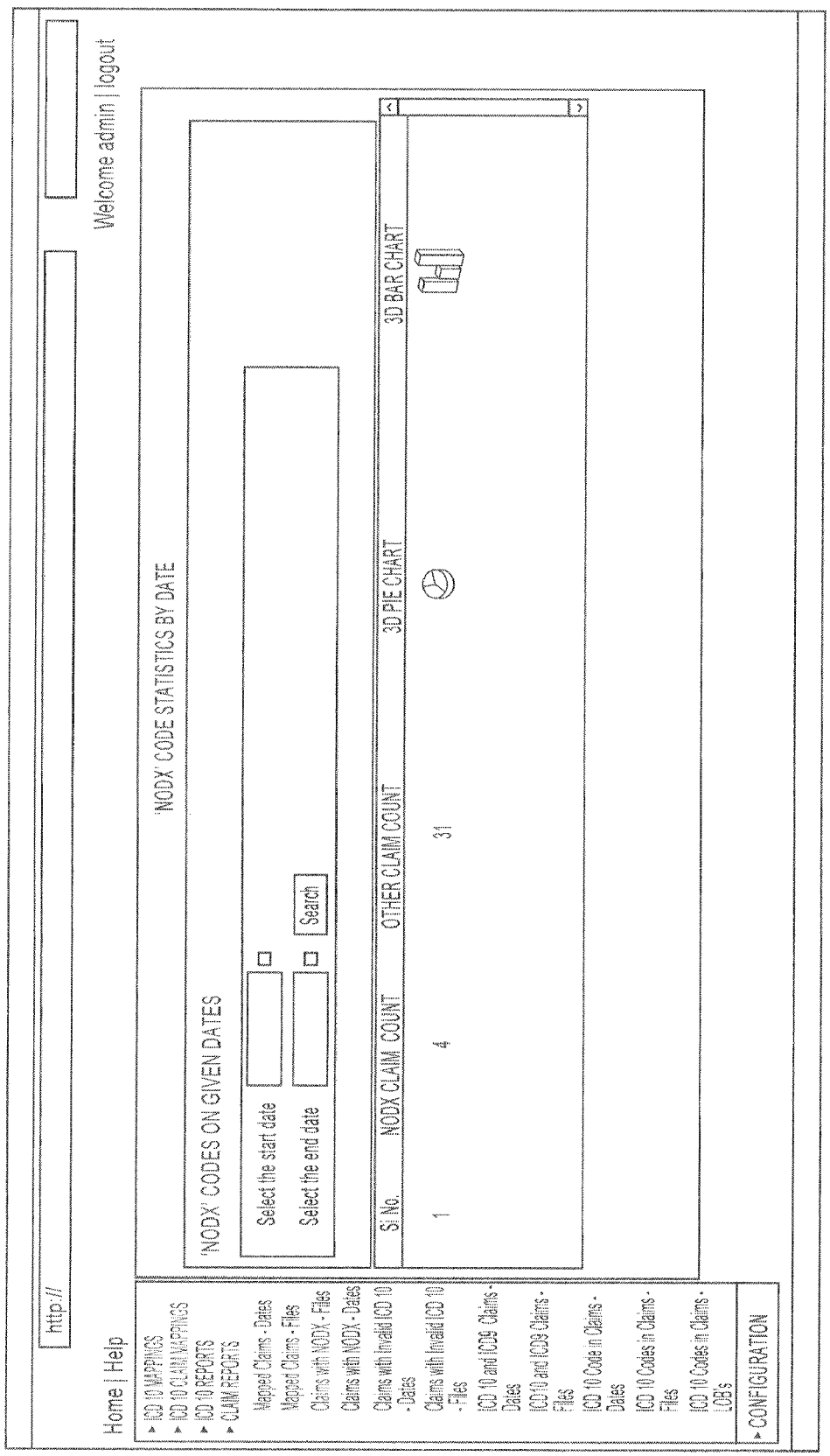
Figure 3T:
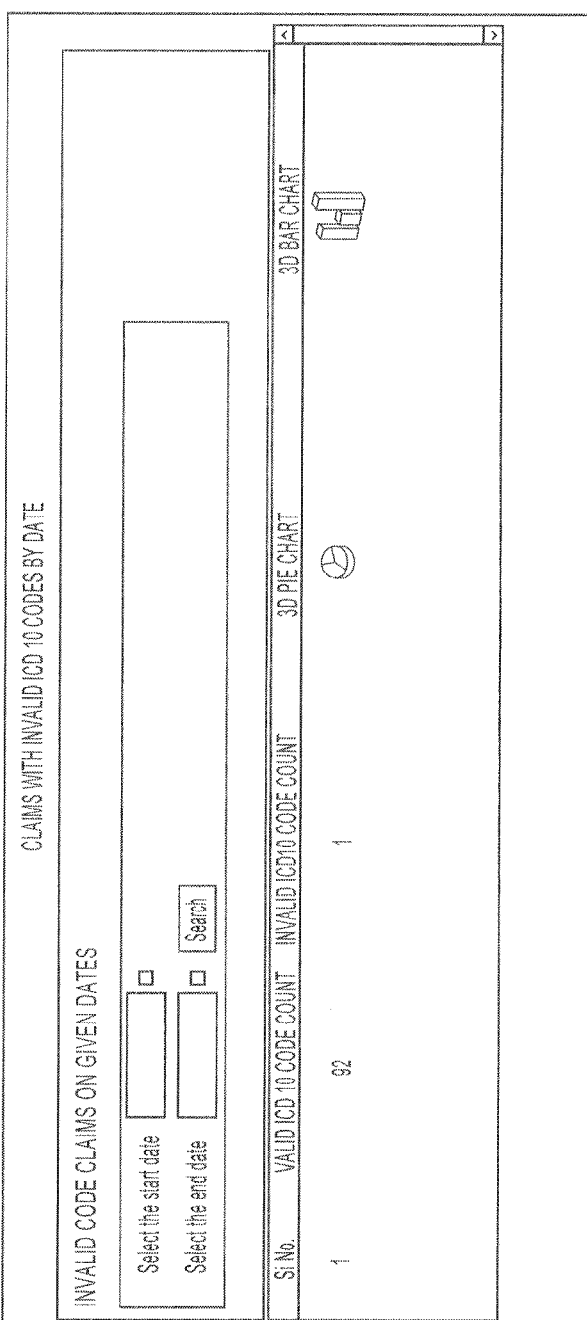

Referring now to FIG. 3A, illustrated is an example GUI screen 300 in accordance with aspects of the present invention. GUI screen 300 may be used for authenticating a user attempting to access the system and providing users access to the system. GUI screen 300 may include data entry boxes for providing a user name 302 and password 304. The user name and password may be authenticated prior to allowing the user access to the system. Users of the system may include, for example, various health care industry constituents (e.g., employers; members; providers; regulatory authorities, both federal and state; and certification agencies), health care services providers (e.g., doctors), and health plan providers (e.g., insurance companies), among other users. It should be appreciated that various users may have various levels of access, depending on the user's security.

Turning now to FIG. 3B, illustrated is an example GUI screen 306 that may be used for displaying various code mappings, e.g., displaying ICD-9 codes that correspond to a given ICD-10 code, in accordance with aspects of the present invention. GUI screen 306 may provide a search box 308 for entering in, for example, an ICD-10 code, one or more radio buttons 312 for selecting whether the code is a diagnosis code or a procedure code, an information box 310 for displaying information relating to the entered code (e.g., a description of the medical condition associated with the entered code), and a selection button 314 for initiating the lookup for the entered code. It should be appreciated that the mapping techniques used for displaying the corresponding ICD-9 codes to the entered ICD-10 codes may be similar to those discussed above in relation to FIGS. 2A-2C.

In addition, GUI screen 306 may include a display 316 with the active mappings for the entered code. For example, display 316 may include the ICD-10 code along with the description of the medical condition associated with the code, the mapping type used for the code, an identification for the user who created the mapping, whether the code mapped to a single code or a group, the effective date of the mapping, and a listing 318 of the mapped codes, among other display information. Listing 318 of the mapped codes may include, for example, the ICD-9 codes that map to the entered ICD-10 code, a priority 320 for each of the mapped ICD-9 codes, and a description for each of the codes. As discussed above, the priority 320 for each of the codes may include, for example, a priority order, e.g., primary codes and secondary codes, a number ranking the codes descending from the highest ranked code to the lowest rank code, or listing indicating which codes are active or inactive, among other prioritization of the codes.

Referring now to FIG. 3C, therein illustrated is an example GUI screen 322 for managing the code mappings, in accordance with aspects of the present invention. GUI screen 322 has similar functionality as GUI screen 306 (FIG. 3B) for entering and searching a code, e.g., an ICD-10 code. Additionally, GUI screen 322 displays the mapping history 324 for the entered code (e.g., tracking the modifications and/or changes made to the code). The mapping history may include, for example, the status of the code, any modifications made to the code mappings, the user who made the modifications, when the modifications occurred, and the current ICD-9 codes that map to the entered code.

In addition, GUI screen 322 also allows a user to add and/or modify code mappings 326 by entering and saving mapping details relating to the entered codes. The user may enter the details relating to the entered code via text boxes, selecting from pop-up menus or drop-down lists, or selecting radio buttons, among other methods of entering and/or selecting data. The user may, for example, add and/or modify one or more of the following: the mapping effective date (e.g., the date the new mapping should start), the method of mapping the codes, code type (e.g., diagnosis or procedure), the mapping status (e.g., active, inactive, loaded), comments or remarks regarding the mapping, and may add or remove ICD-9 codes that map to the entered code. The user may save the changes to the code mappings by selecting the save mapping button 328.

Aspects of the present invention may permit a user to look up claims and display claim information, as illustrated in FIGS. 3D-3F. Turning now to FIG. 3D, therein illustrated is an example GUI screen for allowing the user to look up claim information. The GUI screen may allow the user to enter an ICN number, an AHIN (Advanced Health Information Network) number, a member identification (ID) number, a contract ID, or a provider ID for searching for the claim information 330. The GUI screen may display the resulting claim details 332 from the search. For example, the claim details 332 may include the line of business (LOB) for the claim, the ICN number, the AHIN number, the member ID, the claim sequence number, a claim status code, an input file name for the claim, and an additional file name for the claim, among other claim details. In addition, the GUI screen may display the different mapping details and descriptions 334 for the mapped ICD-10 codes to the ICD-9 codes for the claim.

Aspects of the present invention may permit the user to look up claim information within a given date range, as illustrated by the GUI screen in FIG. 3E. For example, the user may enter a start date and end date 336, or the user may select the start date and end date from a calendar. The GUI screen may display a list of claims 338 and the claim details that fall within the selected date range. Additional aspects of the present invention, may permit the user to look up claims that have been normalized by file name, as illustrated by the GUI screen in FIG. 3F. The user may enter a claim filename 340, and the GUI screen may display a list of claims 342 that have been normalized for the entered filename.

Aspects of the present invention relate to collection of statistically significant data and other information for newly implemented coding/nomenclature, analysis of collected data, and conversion or other normalization of the collected data for comparison with prior coding/nomenclature received data, such that the implementation may be validated/revalidated, calibrated, and/or redefined to meet confidence levels that existed with respect to the prior coding/nomenclature. This data collection can affect such factors as utilization review edits, actuarial forecasting methodologies, and rating methodologies, among others. For these purposes, sufficient data must be collected for each aspect of each plan.

Aspects of the present invention may allow changes in normalization to occur globally (e.g., switching from a prior common nomenclature for normalizing processed information to the newly implemented nomenclature). This process will occur once the "data fog" of partial implementation has sufficiently cleared to render confidence in the newly implemented codes/nomenclature and system for handling.

Referring now to FIGS. 3G-3X, therein illustrated are examples of various GUI screens for different generated reports and analysis based upon the collected normalization data, according to aspects of the present invention. FIG. 3G illustrates an example report displaying a list of ICD-10 codes that are mapped to a particular ICD-9 code. Thus, a user may enter in an ICD-9 code and view a list of the various ICD-10 codes and code details (e.g., code descriptions, code type, mapping effective date, mapping terminal date, the status of the code and any comments relating to the code) that have mapped to the entered ICD-9 code.

FIG. 3H illustrates an example report displaying ICD-10 codes that do not map to an ICD-9 code and/or that map to multiple ICD-9 codes. As illustrated in FIG. 3I, another report may include, for example, displaying the changes performed on an ICD mapping by a selected user. For example, a user may enter a user name and/or select a user name from a drop-down or pop-up menu, and a report may display the changes and/or modifications made by the selected user (e.g., the history of the changes and/or modifications to the ICD mapping will be generated). Another example report may include selecting a date range for searching for changes that have been made to the codes within the specified date range, as illustrated in FIG. 3K. The user may enter a start date and end date, or select the dates through a calendar function, and a list of the changes made to the ICD-10 codes within the selected date range may be generated.

Figure 3U:
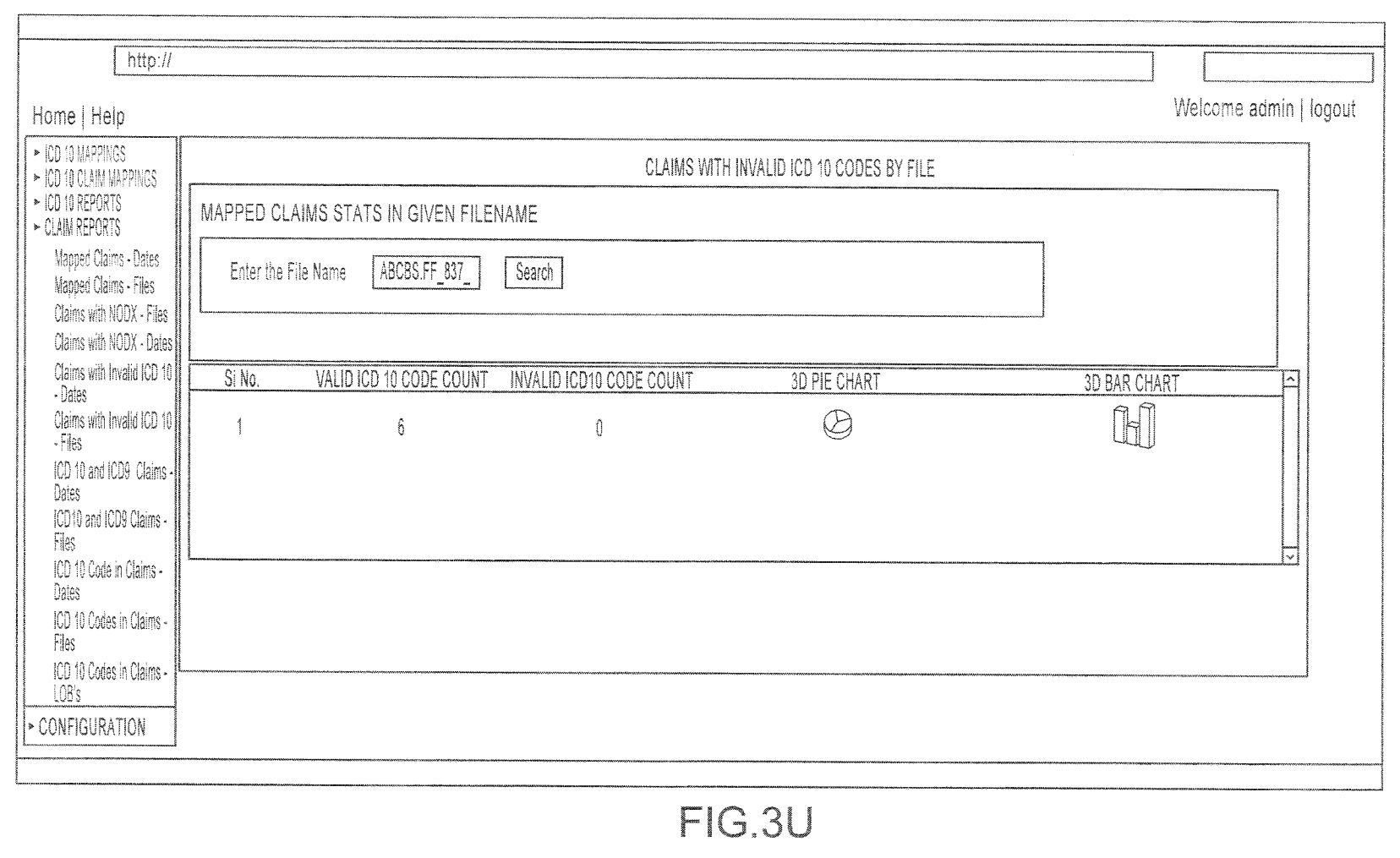
Figure 3V:
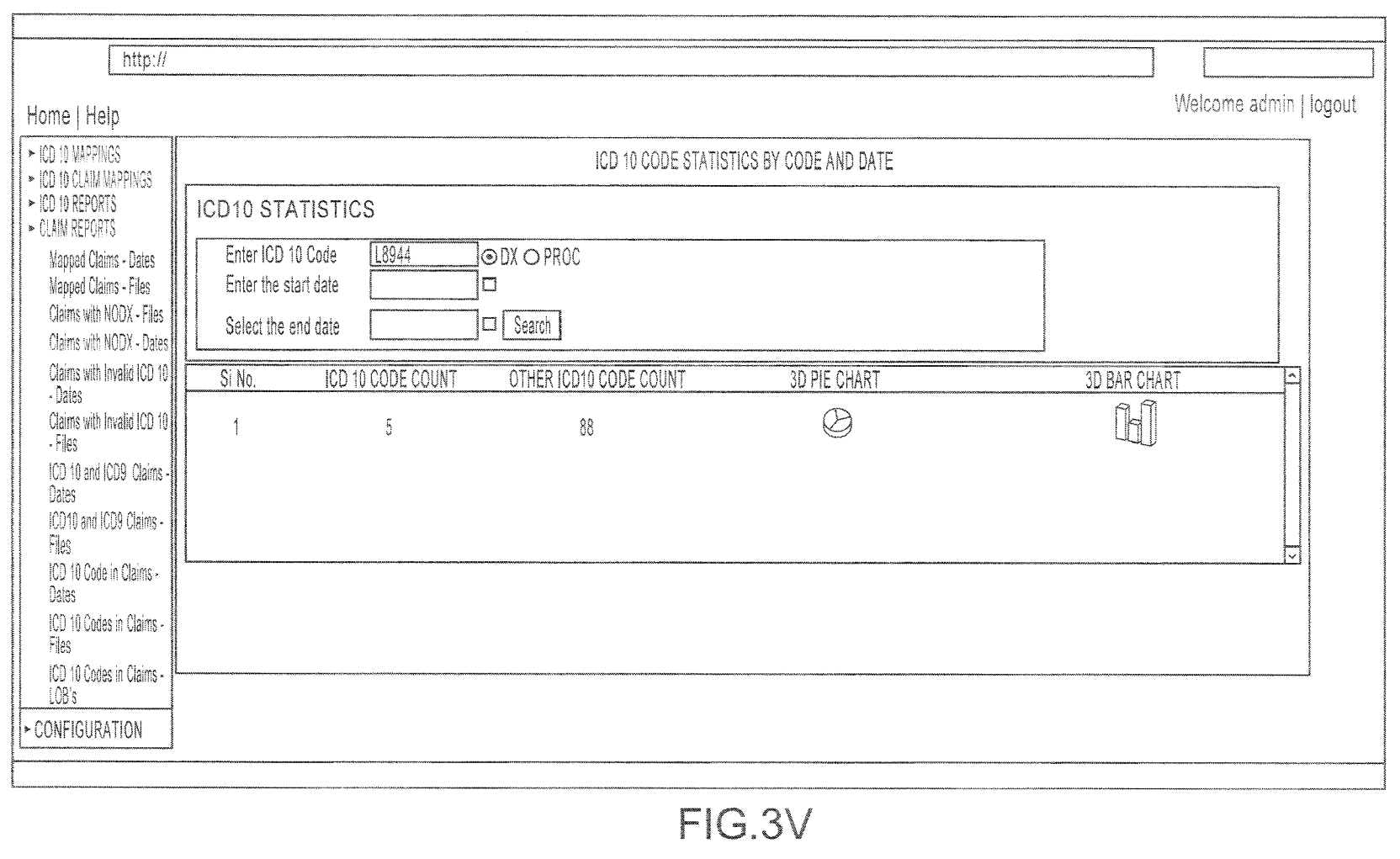
Figure 3W:
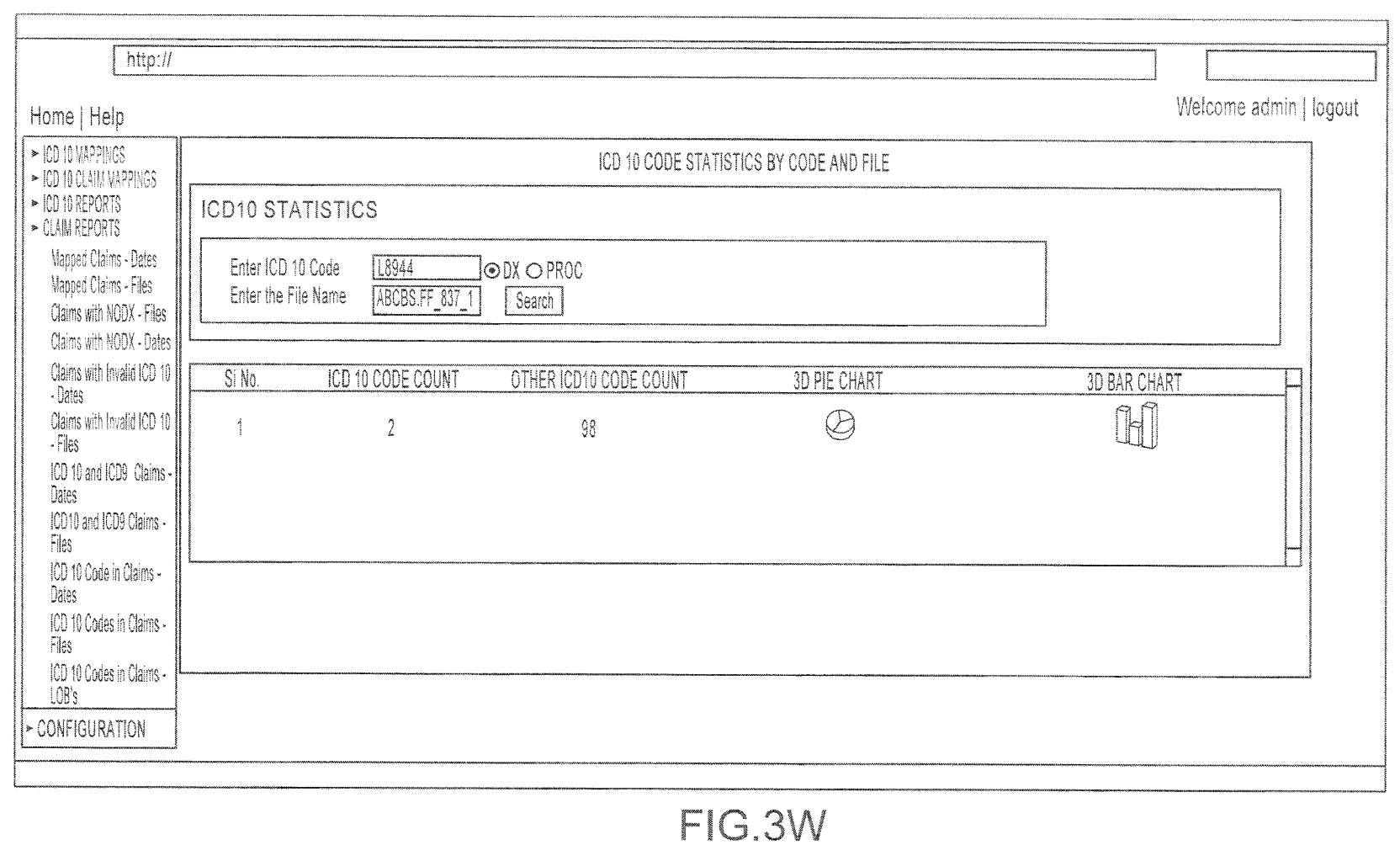

FIG. 3L illustrates another example report for providing a listing of all the ICD-10 codes that have active CMS based mappings. This report may also display the unchanged ICD-10 code mappings with ICD-9 code descriptions. Another example report may include displaying the changes for the ICD-10 codes that do not map to ICD-9 codes, as illustrated in FIG. 3M. Aspects of the present invention may also include a report listing the ICD-10 codes that became and/or will become active on a specified effective dates, as illustrated in FIG. 3N. The user may enter an effective date (e.g., a start date), or select a date from a calendar, and a list of the ICD-10 codes that become and/or will become active on the specified date may be generated.

In addition, aspects of the present invention may provide statistical analysis, e.g., graphs and/or charts, based on the collected data, as illustrated in FIGS. 3O-3X. The statistical analysis may include, for example, analysis based on a specified date range or file name for the following: the status of diagnosis and procedural codes; normalized claims (e.g., the percentage of normalized and non-normalized claims within the specified date range); ICD-10 codes that do not map to ICD-9 codes (e.g., the percentage of ICD-10 codes that have mappings to ICD-9 codes and the percentage of ICD-10 codes that do not have mappings to ICD-9 codes); claims with invalid codes; statics of ICD-10 and ICD-9 codes (e.g., the number of ICD-10 and ICD-9 codes within the selected date range or file name); and/or other factors. Additionally, the statistical analysis may include the number of ICD-10 codes and ICD-9 codes presented in each Line of Business (LOB).

Figure 3Y:
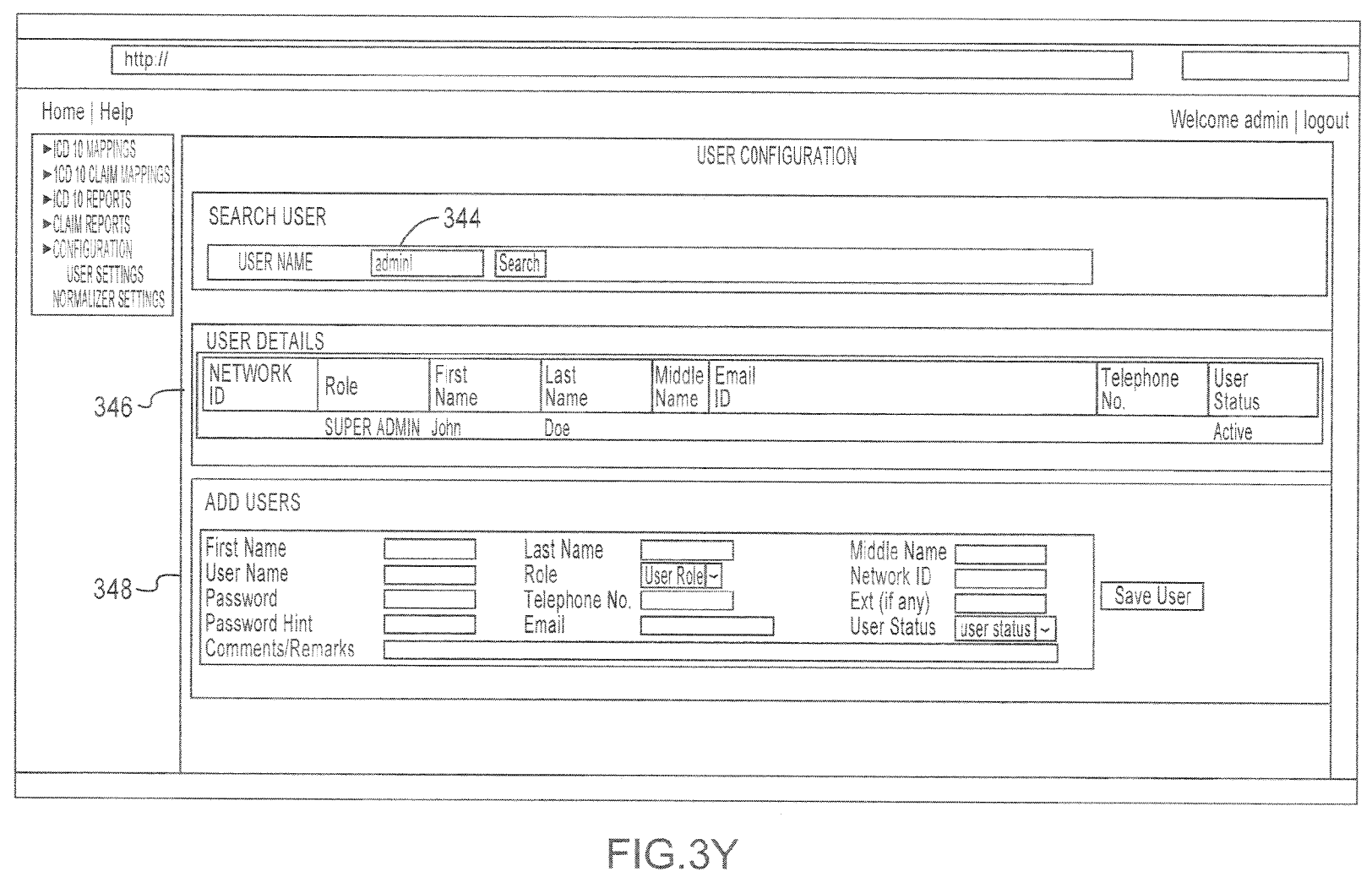

Aspects of the present invention may also include adding and/or managing users, as illustrated by the GUI screen in FIG. 3Y. The GUI screen may allow a user (e.g., an administrator) to enter and search for a user name 344. The GUI screen may display the user's details 346, which may include, for example, the user's network ID, the user's role (e.g., supervisor, administrator), the user's name, the user's contact information (e.g., e-mail address and telephone number), and the user's status (e.g., active, inactive). In addition, the GUI screen may provide the functionality to add a user 348, remove a user, and/or modify the user's information (e.g., modifying the user's role and/or status).

Figure 3Z:
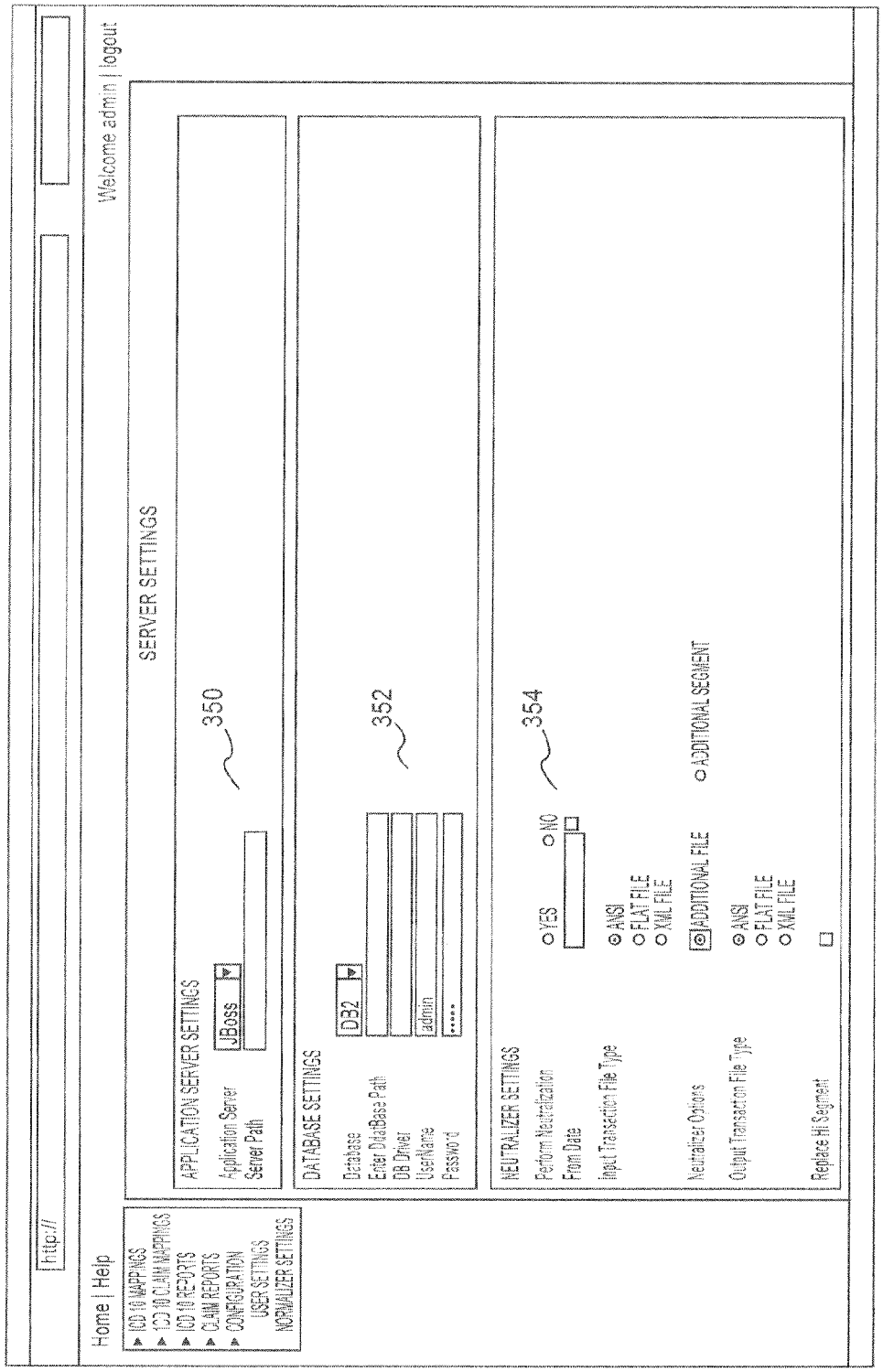

Aspects of the present invention may also include configuring and/or managing a computing system, as illustrated in FIG. 3Z. For example, the user may be able to configure the application server settings 350, the data repository settings 352 and the normalizer settings 354. The normalizer settings 354 may include, for example, scheduling when the normalization may occur, turning on and/or off the normalization functionality, determining the types of data accepted by the system, and determining the types of data the system may transmit, among other settings.

Figure 4:
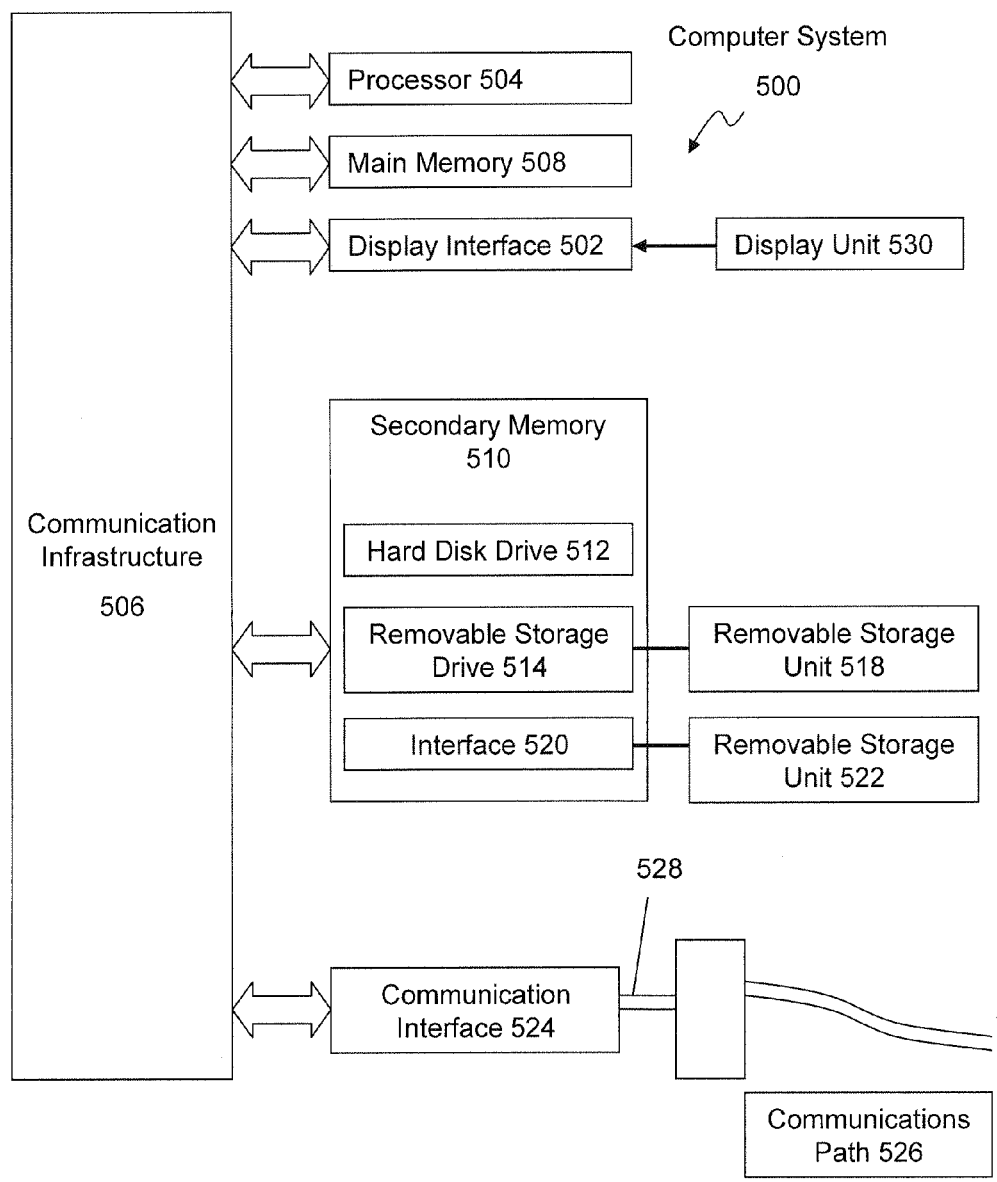
FIG. 4 illustrates various computer hardware and software elements, or combination thereof, with or upon which aspects of the present invention may be implemented.

Aspects of the present invention may be implemented using hardware, software or a combination thereof and may be implemented in one or more computer systems or other processing systems. In one variation, aspects of the present invention are directed toward one or more computer systems capable of carrying out the functionality described herein. An example of such a computer system 500 is shown in FIG. 4.

Computer system 500 includes one or more processors, such as processor 504. The processor 504 is connected to a communication infrastructure 506 (e.g., a communications bus, cross-over bar, or network). Various software aspects are described in terms of this exemplary computer system. After reading this description, it will become apparent to a person skilled in the relevant art(s) how to implement aspects of the present invention using other computer systems and/or architectures.

Computer system 500 can include a display interface 502 that forwards graphics, text, and other data from the communication infrastructure 506 (or from a frame buffer not shown) for display on the display unit 530. Computer system 500 also includes a main memory 508, preferably random access memory (RAM), and may also include a secondary memory 510. The secondary memory 510 may include, for example, a hard disk drive 512 and/or a removable storage drive 514, representing a floppy disk drive, a magnetic tape drive, an optical disk drive, etc. The removable storage drive 514 reads from and/or writes to a removable storage unit 518 in a well-known manner. Removable storage unit 518, represents a floppy disk, magnetic tape, optical disk, etc., which is read by and written to removable storage drive 514. As will be appreciated, the removable storage unit 518 includes a computer usable storage medium having stored therein computer software and/or data.

In alternative variations, secondary memory 510 may include other similar devices for allowing computer programs or other instructions to be loaded into computer system 500. Such devices may include, for example, a removable storage unit 522 and an interface 520. Examples of such may include a program cartridge and cartridge interface (such as that found in video game devices), a removable memory chip (such as an erasable programmable read only memory (EPROM), or programmable read only memory (PROM)) and associated socket, and other removable storage units 522 and interfaces 520, which allow software and data to be transferred from the removable storage unit 522 to computer system 500.

Computer system 500 may also include a communications interface 524. Communications interface 524 allows software and data to be transferred between computer system 500 and external devices. Examples of communications interface 524 may include a modem, a network interface (such as an Ethernet card), a communications port, a Personal Computer Memory Card International Association (PCMCIA) slot and card, etc. Software and data transferred via communications interface 524 may be in the form of signals 528, which may be electronic, electromagnetic, optical or other signals capable of being received by communications interface 524. These signals 528 are provided to communications interface 524 via a communications path (e.g., channel) 526. This path 526 carries signals 528 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 514, a hard disk installed in hard disk drive 512, and signals 528. These computer program products provide software to the computer system 500. Aspects of the present invention are directed to such computer program products.

Computer programs (also referred to as computer control logic) are stored in main memory 508 and/or secondary memory 510. Computer programs may also be received via communications interface 524. Such computer programs, when executed, enable the computer system 500 to perform the features in accordance with aspects of the present invention, as discussed herein. In particular, the computer programs, when executed, enable the processor 504 to perform the features of certain aspects of the present invention. Accordingly, such computer programs represent controllers of the computer system 500.

In one variation where aspects of the present invention are implemented using software, the software may be stored in a computer program product and loaded into computer system 500 using removable storage drive 514, hard drive 512, or communications interface 524. The control logic (software), when executed by the processor 504, causes the processor 504 to perform the functions in accordance with aspects of the present invention, as described herein. In another variation, aspects of the present invention are implemented primarily in hardware using, for example, hardware components, such as application specific integrated circuits (ASICs). Implementation of the hardware state machine so as to perform the functions described herein will be apparent to persons skilled in the relevant art(s).

In yet another aspect of the present invention, the invention is implemented using a combination of both hardware and software.

Figure 5:
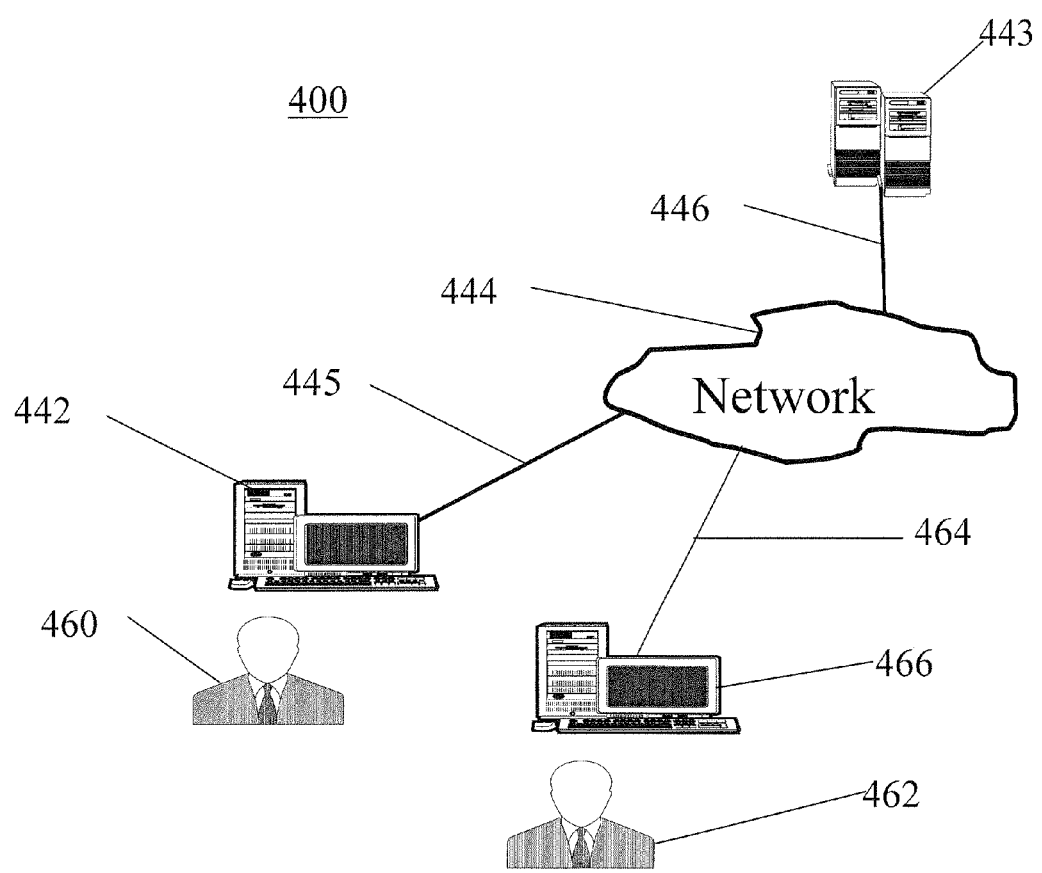
FIG. 5 illustrates an exemplary system diagram of various hardware components and other features, in accordance with aspects of the present invention.

FIG. 5 shows a communication system 400 usable in accordance with aspects of the present invention. The communication system 400 includes one or more accessors 460, 462 (also referred to interchangeably herein as one or more "users") and one or more terminals 442, 466. In one aspect of the present invention, data for use is, for example, input and/or accessed by accessors 460, 464 via terminals 442, 466, such as personal computers (PCs), minicomputers, mainframe computers, microcomputers, telephonic devices, or wireless devices, such as personal digital assistants ("PDAs") or a hand-held wireless devices coupled to a server 443, such as a PC, minicomputer, mainframe computer, microcomputer, or other device having a processor and a repository for data and/or connection to a repository for data, via, for example, a network 444, such as the Internet or an intranet, and couplings 445, 446, 464. The couplings 445, 446, 464 include, for example, wired, wireless, or fiberoptic links. In another aspect of the present invention, the method and system of the present invention operate in a stand-alone environment, such as on a single terminal.

Exemplary aspects of the present invention have now been described in accordance with the above advantages. It will be appreciated that these examples are merely illustrative of the invention. Many variations and modifications will be apparent to those skilled in the art.

The invention claimed is:

1. A method implemented on a suitably programmed computer comprising a processor and a display, the method comprising:

receiving at least one transaction in an International Classification of Diseases (ICD) 9 format or an ICD 10 format;

determining whether the received transaction is in the ICD 9 format or the ICD 10 format;

when the received transaction is in the ICD 10 format, identifying at least one transaction in the ICD 9 format that matches the received transaction in the ICD 10 format;

processing, via the processor, the identified transaction in the ICD 9 format, wherein processing the identified transaction comprises one of processing an eligibility query, processing a claim, and performing claims management;

providing processing results in the ICD 10 format by associating the processed identified transaction in the ICD 9 format with the ICD 10 format; and transmitting the processing results of the processed transaction, wherein identifying at least one transaction in the ICD 9 format that matches the received transaction in the ICD 10 format further comprises:

mapping an ICD 10 code from the received transaction to an ICD 9 code selected from a group of at least one ICD 9 code;

identifying whether the group of ICD 9 codes are in a priority order; and selecting at least a highest priority code from the group of ICD 9 codes for the ICD 9 format, and wherein when the received transaction is in the ICD 9 format, processing, via the processor, the received transaction, providing processing results in the ICD 9 format, and transmitting the processing results of the processed transaction.

2. The method of claim 1, wherein the priority order includes one of a primary and secondary codes, a ranking descending from a highest code to a lowest code, and active and inactive codes.

3. The method of claim 1, further comprising:
generating a report based upon the processing results, the ICD 10 format and the ICD 9 format.

4. The method of claim 3, wherein generating the report includes performing statistical analysis on the processing results, the ICD 10 format and the ICD 9 format.

5. The method of claim 1, further comprising:
determining whether an error occurred during receipt of the transaction; and
displaying an error message if the error occurred during receipt of the transaction.

6. The method of claim 5, wherein the error comprises an invalid code and an improperly entered code.

7. The method of claim 1, wherein identifying at least one transaction in the ICD 9 format that matches the received transaction in the ICD 10 format further comprises:
prompting a user to select at least one ICD 9 code for the ICD 9 format.

8. The method of claim 1, further comprising:
when no transactions in the ICD 9 format matches the received transaction in the ICD 10 format, identifying each of the unidentified transactions in the ICD 10 format.

9. The method of claim 1, wherein at least one transaction is a medical claim.

10. A system comprising:
computer elements receiving at least one transaction in an International Classification of Diseases (ICD) 9 format or an ICD 10 format;
computer elements determining whether the received transaction is in the ICD 9 format or the ICD 10 format;
when the received transaction is in the ICD 10 format, means for computer elements identifying at least one transaction in the ICD 9 format that matches the received transaction in the ICD 10 format;
computer elements processing the identified transaction in the ICD 9 format, wherein processing the identified transaction comprises one of processing an eligibility query, processing a claim, and performing claims management;
computer elements providing processing results in the ICD 10 format by associating the processed identified transaction in the ICD 9 format with the ICD 10 format; and
computer elements transmitting the processing results of the processed transaction,
wherein identifying at least one transaction in the ICD 9 format that matches the received transaction in the ICD 10 format further comprises:
computer elements mapping an ICD 10 code from the received transaction to an ICD 9 code selected from a group of at least one ICD 9 code;
computer elements identifying whether the group of ICD 9 codes are in a priority order; and
computer elements selecting at least a highest priority code from the group of ICD 9 codes for the ICD 9 format, and
wherein when the received transaction is in the ICD 9 format, computer elements processing the received transaction, computer elements providing processing results in the ICD 9 format, and computer elements transmitting the processing results of the processed transaction.

11. The system of claim 10, wherein the priority order includes one of a primary and secondary codes, a ranking descending from a highest code to a lowest code, and active and inactive codes.

12. The system of claim 10, further comprising:
computer elements generating a report based upon the processing results, the ICD 10 format and the ICD 9 format.

13. The system of claim 12, wherein generating the report includes computer elements performing statistical analysis on the processing results, the ICD 10 format and the ICD 9 format.

14. The system of claim 10, further comprising:
computer elements determining whether an error occurred during receipt of the transaction; and
computer elements displaying an error message if the error occurred during receipt of the transaction.

15. The system of claim 14, wherein the error comprises an invalid code and an improperly entered code.

16. The system of claim 10, wherein identifying at least one transaction in the ICD 9 format that matches the received transaction in the ICD 10 format further comprises:
computer elements prompting a user to select at least one ICD 9 code for ICD 9 format.

17. The system of claim 10, further comprising:
when no transaction in the ICD 9 format matches the received transaction in the ICD 10 format, computer elements identifying each of the unidentified transactions in the ICD 10 format.

18. The system of claim 10, wherein at least one transaction is a medical claim.

19. A computer program product comprising a non-transitory computer usable medium having control logic stored therein for causing a computer to process transaction, the control logic comprising:
computer readable program code means for receiving at least one transaction in an International Classification of Diseases (ICD) 9 format or an ICD 10 format;
computer readable means for determining whether the received transaction is in the ICD 9 format or the ICD 10 format;
when the received transaction is in the ICD 10 format, computer readable means for identifying at least one transaction in the ICD 9 format that matches the received transaction in the ICD 10 format;
computer readable program code means for processing the identified transaction in the ICD 9 format, wherein processing the identified transaction comprises one of processing an eligibility query, processing a claim, and performing claims management;
computer readable program code means for providing processing results in the ICD 10 format by associating the processed identified transaction in the ICD 9 format with the ICD 10 format; and
computer readable program code means for transmitting the processing results of the processed transaction,
wherein identifying at least one transaction in the ICD 9 format that matches the received transaction in the ICD 10 format further comprises:
computer readable program code means for mapping an ICD 10 code from the received transaction to an ICD 9 code selected from a group of at least one ICD 9 code;
computer readable program code means for identifying whether the group of ICD 9 codes are in a priority order; and computer readable program code means for selecting at least a highest priority code from the group of ICD 9 codes for the ICD 9 format, and
    wherein when the received transaction is in the ICD 9 format, computer readable program code means for processing the received transaction, computer readable code means for providing processing results in the ICD 9 format, and computer readable program code means for transmitting the processing results of the processed transaction.

\* \* \* \* \*